US011837350B2

(12) United States Patent
Crutchfield et al.

(10) Patent No.: US 11,837,350 B2
(45) Date of Patent: Dec. 5, 2023

(54) SYSTEM AND METHOD OF TREATMENT FOR CORRECTING TOOTH MALOCCLUSIONS

(71) Applicant: Clear Blue Smiles LLC, Chantilly, VA (US)

(72) Inventors: William E. Crutchfield, Fairfax, VA (US); Kevin J. Dillard, Wildwood, MO (US); Brian R. Gaudreault, Nantucket, MA (US)

(73) Assignee: CLEAR BLUE SMILES LLC, Chantilly, VA (US)

(*) Notice: Subject to any disclaimer, the term of this patent is extended or adjusted under 35 U.S.C. 154(b) by 57 days.

(21) Appl. No.: 17/235,424

(22) Filed: Apr. 20, 2021

(65) Prior Publication Data

US 2022/0331062 A1    Oct. 20, 2022

(51) Int. Cl.
*G16H 20/40* (2018.01)
*A61C 7/00* (2006.01)
(Continued)

(52) U.S. Cl.
CPC ............ *G16H 20/40* (2018.01); *A61C 7/00* (2013.01); *A61C 7/002* (2013.01); *G16H 10/60* (2018.01);
(Continued)

(58) Field of Classification Search
CPC ..... A61C 7/002; A61C 7/08; A61C 2007/004; G16H 10/60; G16H 20/40; G16H 80/00
See application file for complete search history.

(56) References Cited

U.S. PATENT DOCUMENTS 10,206,759 B2  2/2019  Salah et al.
10,342,645 B2  7/2019  Salah et al.
(Continued)

FOREIGN PATENT DOCUMENTS

JP    2018527997 A    9/2018
KR   20190140990 A   12/2019
(Continued)

OTHER PUBLICATIONS

Lindsey et al., Orthodontists' and parents' perception of finished occlusion and willingness to extend treatment time, Dec. 2020, American Journal of Orthodontics and Dentofacial Orthopedics, vol. 158, Issue 6, pp. 799-806. (Year: 2020).*

(Continued)

*Primary Examiner* — Christopher L Gilligan
(74) *Attorney, Agent, or Firm* — MILES & STOCKBRIDGE P.C.; David R. Schaffer

(57) ABSTRACT

The method and system provides a variable platform for Virtual Reality Orthodontics (VRO), which can be provided virtually to a patient without the patient having to be examined, in-person, by a dentist or orthodontist. Treatment can be rendered that includes clear aligner therapy, wire therapy or a hybrid/combo treatment involving both to treat patients' malocclusions in a virtual setting as opposed to the patients being treated in traditional and conventional orthodontic care facilities, requiring less in-office visits by the patients. The method and system utilizes and embraces dental professionals for patient care to assist licensed dental professionals to provide treatment while under the scrutiny of orthodontists. Patient care and progress can be monitored with the assistance of artificial intelligence and by review of dental professionals.

21 Claims, 12 Drawing Sheets

(51) Int. Cl.
*G16H 10/60* (2018.01)
*A61C 7/08* (2006.01)
*G16H 80/00* (2018.01)

(52) U.S. Cl.
CPC ....... *G16H 80/00* (2018.01); *A61C 2007/004* (2013.01)

(56) References Cited

U.S. PATENT DOCUMENTS

| | | |
|---|---|---|
| 10,417,774 B2 | 9/2019 | Salah et al. |
| 10,485,638 B2 | 11/2019 | Salah et al. |
| 10,588,501 B2 | 3/2020 | Salah et al. |
| 10,685,259 B2 | 6/2020 | Salah et al. |
| 10,736,715 B2 | 8/2020 | Salah et al. |
| 10,755,409 B2 | 8/2020 | Salah et al. |
| 10,779,909 B2 | 9/2020 | Salah et al. |
| 10,799,321 B2 | 10/2020 | Salah et al. |
| 10,842,592 B2 | 11/2020 | Salah et al. |
| 10,966,667 B2 | 4/2021 | Salah et al. |
| 2014/0329194 A1 | 11/2014 | Sachdeva et al. |
| 2017/0056131 A1 | 3/2017 | Alauddin et al. |
| 2017/0325690 A1 | 11/2017 | Salah et al. |
| 2018/0185125 A1 | 7/2018 | Salah et al. |
| 2018/0204332 A1 | 7/2018 | Salah et al. |
| 2018/0344430 A1 | 12/2018 | Salah et al. |
| 2018/0353263 A1 | 12/2018 | Salah et al. |
| 2019/0026598 A1 | 1/2019 | Salah et al. |
| 2019/0026599 A1 | 1/2019 | Salah et al. |
| 2019/0026893 A1 | 1/2019 | Salah et al. |
| 2019/0026894 A1 | 1/2019 | Salah et al. |
| 2019/0105129 A1 | 4/2019 | Salah |
| 2019/0125493 A1 | 5/2019 | Salah et al. |
| 2020/0000554 A1* | 1/2020 | Makarenkova ........ A61C 7/002 |
| 2020/0066391 A1* | 2/2020 | Sachdeva ................ A61C 7/08 |
| 2020/0170755 A1* | 6/2020 | Kumamoto ............. A61C 9/00 |
| 2020/0234354 A1* | 7/2020 | Breeland ............... G06Q 30/06 |
| 2020/0261186 A1* | 8/2020 | Hunter .................... A61C 7/08 |
| 2020/0334813 A1 | 10/2020 | Salah et al. |
| 2020/0405447 A1 | 12/2020 | Salah et al. |
| 2021/0007834 A1 | 1/2021 | Salah et al. |
| 2021/0045858 A1 | 2/2021 | Salah et al. |
| 2021/0298874 A1* | 9/2021 | Katzman ............... G16H 10/60 |

FOREIGN PATENT DOCUMENTS

| | | | |
|---|---|---|---|
| KR | 102240932 B1 | 4/2021 | |
| WO | WO-2019014026 A1 * | 1/2019 | ............ A61C 7/002 |

OTHER PUBLICATIONS

International Search Report dated Jul. 25, 2022 for corresponding PCT Application No. PCT/IB2022/053641.
Written Opinion of the International Searching Authority dated Jul. 25, 2022 for corresponding PCT Application No. PCT/IB2022/053641.

* cited by examiner

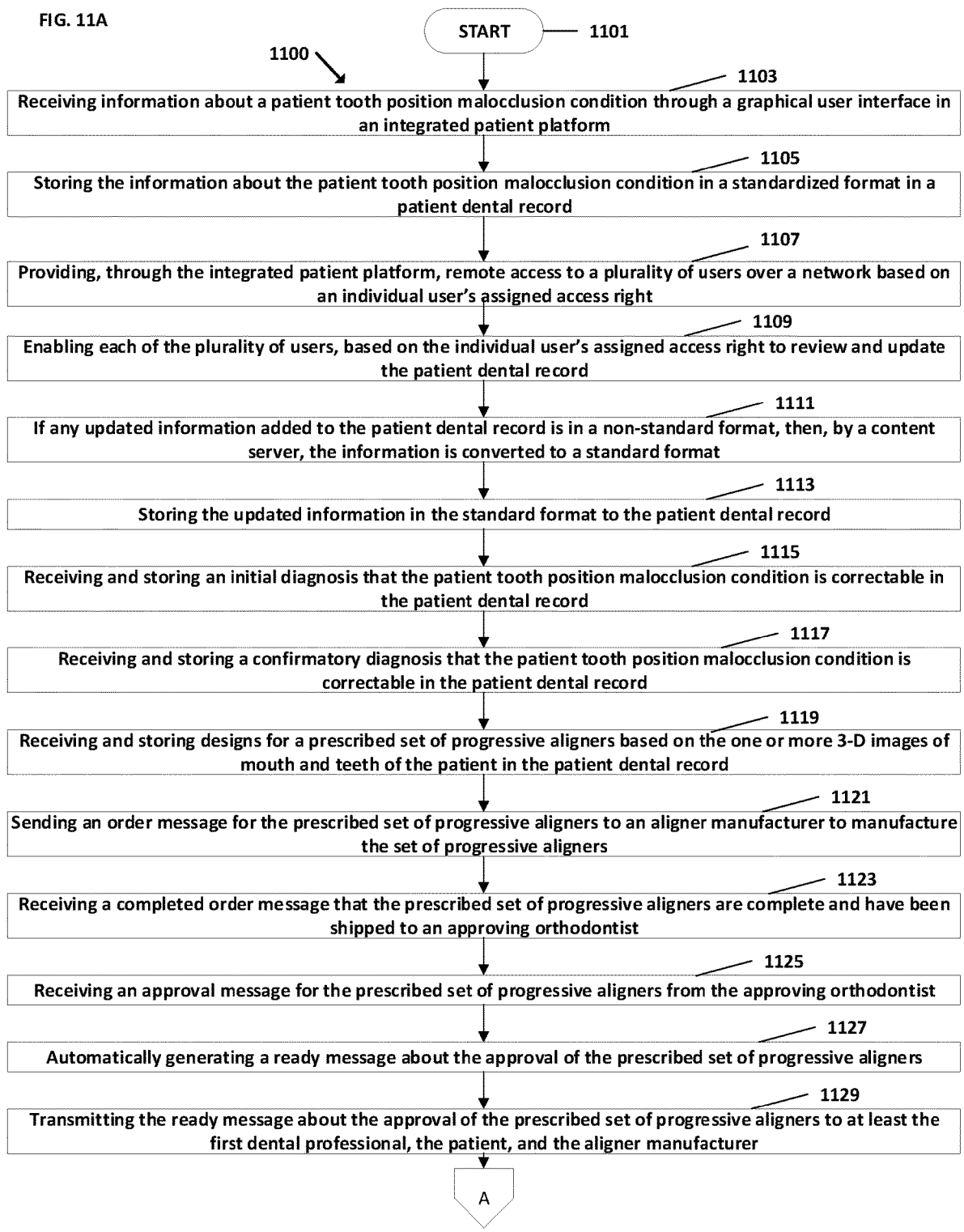

SYSTEM AND METHOD OF TREATMENT FOR CORRECTING TOOTH MALOCCLUSIONS

TECHNICAL AREA

The method and system relate generally to the treatment of tooth malocclusions and more specifically to methods and systems that use an integrated platform for Virtual Reality Orthodontics (VRO) to provide clear aligner therapy, wire therapy, or a hybrid/combination treatment involving both therapies to treat patients' tooth malocclusions.

BACKGROUND

Patients with correctable minor as well as major tooth malocclusions often do not have easy access to the necessary dental care or must visit several different dental professionals for diagnosis and treatment, for example, dentists and orthodontists. Even if available, these dental professionals may be physically separate from each other and unaware of each other. During a visit, each dental professional records information about the patient's condition in his or her own local patient records. These records are often stored locally on a computer in a non-standard format selected by whichever hardware or software platform is in use in the dental professional's local office. As a result, it is difficult for dental professionals to share updated information about a patient's condition with other dental professionals using current patient management systems, due to the above challenges. This can lead to problems with being able to accurately diagnose and treat a patient's tooth position malocclusions. In addition, unfortunately, a qualified dental professional may not be conveniently, physically located in and not able to serve every area in the country. As a result, the availability of a specific level of needed dental care in certain areas of the country can be limited.

Regardless, generally, a patient's dentist first identifies the patient as having a tooth malocclusion. The dentist may or may not provide orthodontics care, and if not offering orthodontics care the dentist will refer the patient to a licensed orthodontist for their care. In addition, the timely sharing and updating of medical records between the dentist and the patient's orthodontist is vital for consistent, quality care, and to provide both the dentist and the orthodontist with the patient's up to date medical records. Unfortunately, the normal physical separation between the patient's dentist and orthodontist can lead to incomplete records regarding the patient's current dental care/status because records are not timely or readily-shared or cannot be consolidated due to format inconsistencies between the dentist's and the orthodontist's patient record keeping systems. Therefore, a method and system is needed to permit the sharing of dental information between various dental professionals and to enable the referral, onboarding, diagnosis and treatment of patient with tooth malocclusions, regardless of the location of the patient.

SUMMARY

To address the above-described problem, embodiments of the subject network-based patient tooth malocclusion diagnosis and treatment method and system were developed to collect, convert, consolidate, and share patient information from various dental professionals and dental service and appliance providers in at least one standardized format, store it in network-based storage devices, and provide access to the dental professionals and/or patients to the patient information. This will enable accurate diagnosis and treatment of each patient's unique and specific malocclusion condition. The method and system provides a graphical user interface (GUI) through a content server platform, which can be hardware or a combination of both hardware and software and can be integrated with or independent from the content server platform. A user, for example, but not limited to, a dental professional, such as a dentist, orthodontist, and various dental service providers, is given a user-specific level of access to the platform through the GUI to enter, view or update information about a patient's medical condition using the user's own local device (e.g., but not limited to, a personal computer, laptop, tablet, or other wireless handheld device) based on the user's specific level of access. The access can either be from a local location, that is, in an adjacent or close physical location, or a remote location, that is, in a different, distant physical location to the platform. When the user wants to update the patient's records, the user can input the update via the user's chosen device directly into the platform. Whenever the patient information is updated, it is stored in a collection of patient medical records on one or more of the network-based storage devices. After the updated information about the patient's condition has been stored in the collection of patient medical records, the content server, which is connected to the network-based storage devices, immediately generates a message containing either a notice about or the actual updated information about the patient's condition. This message is selectively transmitted over the computer network to all dental professionals, dental service, and appliance providers that have access to and need to know the patient's updated information via the platform. This ensures that each of the necessary dental professionals and dental service and appliance providers is always provided immediate notice and access to changes so they can readily adapt their own medical diagnostic and treatment strategy in accordance with other providers' actions. The message can be in the form of an email message, text message, or other type of message known in the art. Regardless, of whether the dental professional or dental service and appliance providers notice or read the message, the updated information is already stored in the collection of patient medical records, so it is available to all authorized users.

BRIEF DESCRIPTION OF THE DRAWINGS

Non-limiting and non-exhaustive embodiments of the presently disclosed subject matter are described with reference to the following figures, wherein like reference numerals and/or indicia refer to like parts throughout the various views unless otherwise precisely specified.

FIGS. 11A and 11B are a flow chart diagram of a patient diagnostic and treatment method 1100, in accordance with various embodiments of the disclosed subject matter.

DETAILED DESCRIPTION

Figure 1:
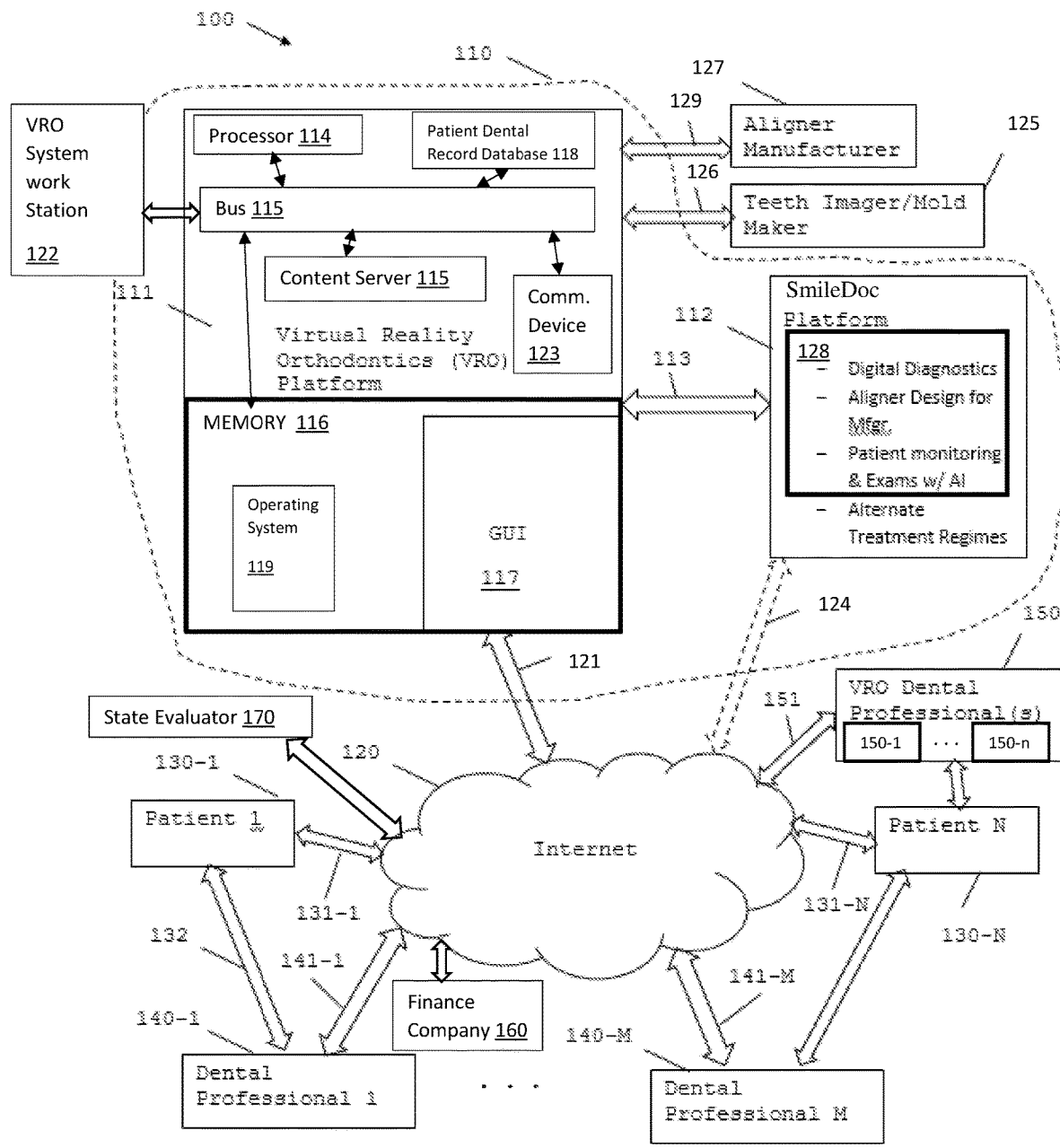
FIG. 1 is a block system diagram showing a configuration of a Virtual Reality Orthodontics (VRO) system illustrating the system components, users, and communication paths there between, in accordance with various embodiments of the disclosed subject matter.

The presently disclosed subject matter pertains to integrated systems and methods for the diagnosis of a patient's correctable tooth position malocclusions, which is also referred to as a patient's correctable tooth position abnormalities, by a first dental professional based on a physical exam or a virtual exam of the patient's teeth, confirming the diagnosis of the patient's correctable tooth position malocclusions by a second dental professional, prescribing a treatment plan to correct the patient's correctable tooth position malocclusions, creating a digital design for a prescribed set of aligners by the first dental professional or the second dental professional to correct the patient's correctable tooth position malocclusions, sending the digital design for the prescribed set of aligners to an aligner manufacturer to fabricate the prescribed set of aligners, receiving and approving the prescribed set of aligners by an orthodontist, sending the prescribed set of aligners to the patient for wearing according to the prescribed plan, regularly monitoring the patient during the course of the prescribed treatment plan, All of the above can be performed through the use of a single, integrated virtual reality orthodontics (VRO) system. The VRO system provides secure and consistent information, rapid updates of patient information, rapid and secure communications, a central location for all patient information, and easy access by all authorized dental professionals and providers.

In general, the integrated systems and methods are implemented in and operate through the integrated VRO system, which includes a VRO platform connected to a patient management platform, and provides an interface with features that integrate all of the necessary, separate, and disconnected doctor and service provider systems that are currently used into a novel, one-stop system for referring, onboarding, financing/paying for the treatment, diagnosing and prescribing treatment, designing the prescribed set of aligners, manufacturing the prescribed set of aligners to treat the patient, reviewing and approving the manufactured prescribed set of aligners by an orthodontist, providing and treating the patient with the prescribed set of aligners, and monitoring the patient during treatment to include conducting virtual and/or physical examinations of the patient's progress.

Specific benefits of the presently disclosed system and method over existing, disconnected systems include, but are not limited to: improved speed of communications and increased access to up-to-date patient information due to the integrated communications and central data storage; all dental professionals have access to and can update a patient's dental information through a single, integrated platform; and the patient's dental information is stored in a central database that is accessible by authorized users of the system. In addition, related service professionals such as aligner manufacturers, scan centers, finance companies, and billing professionals as well as patients can have access to the system to enter and retrieve information to which they have authorization to access. A further benefit is that patients can have a virtual appointment with a doctor through the system using video communications equipment/systems, which can include for example, currently available commercial systems such as Zoom® and Goto Meeting®, as well as, a specially programmed and integrated proprietary video communications equipment/system that is part of the presently disclosed system and method. A related benefit is that all information added to the patient's dental record is immediately available to all other dental professionals that have access to the patient's dental information.

Another benefit of the presently disclosed system and method is improved currency, completeness, accuracy of and access to each patient's dental information, because all authorized dental professionals involved in treating the patient can access and update the patient's dental information through the single, integrated patient platform and all of the patient's dental information is stored in the central database. A further benefit is an improvement in the quality of treatment and care of the patient, because an originating doctor's diagnosis of a patient having a correctable tooth malocclusion is reviewed and confirmed by a second, independent doctor, and the actual manufactured aligners are physically reviewed and approved by an orthodontist before they are provided to the patient for treatment. If not approved, the aligners are sent back to the aligner manufacturer to remanufacture them. A still further benefit is that presently disclosed system and method improves efficiency in providing patient care, because all of the patient's dental information related to this treatment is stored in the patient's dental record in the central database to which only the patient's authorized dental professionals have access. For example, the patient's dental information can include, but is not limited to, the patient's complete dental history including doctor's treatment notes, x-rays, bite wings, digital scans, photographs or scanned images of physical, negative dental impressions made with a dental impression material, for example, but not limited to, polyvinyl siloxane (PVS), direct digital scans of the mouth and teeth of the patient (i.e., intraoral scans), etc.

Yet another benefit of the presently disclosed system and method is an improved availability of treatment to patients that do not live close to a trained dental professional capable of providing this kind of treatment. In addition, it improves patient access through the platform to their personal dental information, improves and streamlines the payment and financing process and doctor collections, because the patient can apply directly for financing through the system with multiple lenders, receive and distribute loan disbursements, make manual payments, and set up automatic payments. Similarly, the integrated platform system improves efficiency for the doctors, patients, and service providers by having a single access point for all needed services, which can result in increased job satisfaction and satisfaction with the treatment.

A still further benefit includes providing multiple options for how patients can be on-boarded, i.e., brought into the system for treatment, for example, Direct to Provider (DTP), which is where a patient is recruited through, for example, but not limited to, direct marketing efforts and enters into the VRO system without a referral from a treating doctor, for example, a dentist, an orthodontist, an endodontist, a prosthodontist, an oral surgeon, and a periodontist. In this instance, the patient, through the VRO system, registers and creates a patient dental record, then enters their dental information and photos of their mouth and teeth into the patient dental record in a secure, artificial intelligence (AI) system, for example, but not limited to, an existing system like SmileMate™ from Dental Monitoring. After the patient has entered their dental information and photos of their mouth and teeth, a VRO orthodontist, through the VRO system, accesses and uses the secure, AI system to determine whether the patient qualifies for treatment, including whether the patient has a healthy dentition or a healthy mouth, using a patient dental report with a proposed length of treatment and cost generated by the secure, AI system. A healthy dentition, a healthy dental status, a healthy mouth, or good dental health, means that the teeth and gums are free of infections, diseases, injuries, and other problems. If the patient qualifies for treatment, the VRO orthodontist, through the VRO system, sends a message to the patient to go to an affiliated dental professional or an affiliated dental scan center (who is paid by VRO) to have their mouth imaged. The VRO orthodontist also sends a request message to the affiliated dental professional to let them know the patient will be coming and to obtain the patient's initial dental record information, including, but not limited to, digital 3-dimensional molds of the patient's teeth and mouth. Once the patient's initial dental record information is collected, the affiliated dental professional sends the patient's initial dental record information to the VRO orthodontist, through the VRO system, where it is stored in the patient dental record in the central database in a memory of the integrated platform. The central database is connected to and accessible by a connected practice management system (PMS) platform, for example, but not limited to, an existing system like GreyFinch from GreyFinch, LLC. The patient, through the VRO system, is also able to set up an account with a payment and loan processing provider, for example, but not limited to, GreenSky, LLC. The VRO orthodontist, using a 3-dimensional digital treatment planning platform, for example, but not limited to, SureSmile from Dentsply Sirona, that is accessed through the VRO system diagnoses, creates a prescribed treatment plan, and creates a three-dimensional (3-D) digital design for a set of progressive aligners to treat the patient's tooth position malocclusions. Once finalized, the VRO orthodontist sends a patient case file with the diagnosis, the prescribed treatment plan, and the 3-D digital design for the patient's set of progressive aligners through the VRO system to a second orthodontist for quality control to review and confirm the VRO orthodontist's diagnosis, the 3-D digital design for the patient's set of progressive aligners, and the prescribed treatment plan. If approved, the second orthodontist sends the patient case file, through the VRO system, to a state evaluator 170 for final approval. The state evaluator 170 is a licensed and highly trained dental professional, for example, but not limited to, an orthodontist with training and extensive experience in the use of 3-D digital dental diagnostic, treatment planning, and orthodontic appliance and aligner design and manufacturing. The state evaluator can be a non-VRO orthodontist as well as one or more of the VRO orthodontists.

Once the VRO orthodontist receives the final approval back from the state evaluator 170, through the VRO system, the VRO orthodontist sends an order, also through the VRO system, to an aligner manufacturer to manufacture the patient's set of progressive aligners using the 3-D digital design for the patient's set of progressive aligners. Once completed, the aligner manufacturer sends a message, through the VRO system, to the VRO orthodontist and an aligner approving orthodontist that the aligners are ready and ships the patient's set of progressive aligners to the aligner approving orthodontist to be reviewed and approved before being sent to the patient. If the aligners are approved, the aligner approving orthodontist sends a message that the aligners are ready to the patient and the VRO orthodontist, through the VRO system, and ships the patient's set of progressive aligners along with written, photo, and video instructions on how to insert and wear the patient's set of progressive aligners along with an AI monitoring device directly to patient. The AI monitoring device can include, for example, but is not limited to, a personal mobile phone, tablet, digital camera, and any other dental scanner.

If the aligners are not approved, the aligners are returned to the aligner manufacturer with instructions on what needs to be corrected and messages about the needed corrections are send to the VRO orthodontist and the aligner manufacturer, through the VRO system. Once the corrections have been made the aligner manufacturer sends a new message, through the VRO system, to the VRO orthodontist and the aligner approving orthodontist that the corrected aligners are ready and then sends the patient's corrected set of progressive aligners to an approving orthodontist to be reviewed and approved before being sent to the patient. If the corrected aligners are approved, the aligner approving orthodontist sends a message that the aligners are ready to the patient and the VRO orthodontist, through the VRO system, and ships the patient's set of progressive aligners along with written, photo, and video instructions on how to insert and wear the patient's set of progressive aligners and the above-described, or other, AI monitoring device directly to patient.

During an active treatment phase where the patient is wearing the prescribed aligners for a prescribed time each day, the patient can be monitored for progression analysis by the VRO orthodontist, through the VRO system using the AI monitoring device. If needed, the patient can be directed to the state evaluator 170 for a physical or virtual visit for progression analysis. Once the prescribed treatment plan is completed, the patient will be shipped one or more retention devices with written, photo, and video instructions, i.e., a final aligner that is designed to maintain a final tooth position achieved by the prescribed treatment plan. The one or more retention devices was designed as part of the prescribed treatment plan.

Alternatively, if a patient already has a doctor (e.g., a General Practice dentist who is or may not be trained or equipped to perform some or all of the aligner treatment, one of the affiliated dental professionals, or the affiliated dental scan centers), for a fee, the doctor can place the patient into the VRO system and use the VRO platform and method of treatment for the patient. In yet another alternative, doctors can refer their patients to the VRO doctors to handle the entire treatment process, as described above, and the referring doctor can receive compensation for the referral, but is still able to monitor the patient's progress during the treatment process. This can positively affect both the patient's ultimate treatment and the referring doctor's income with a minimal time and out-of-pocket expense commitment for the referring doctor, because it can free up the referring doctor's in-office resources and time to see other patients with conditions in line with the referring doctor's practice.

Additional advantages of the presently disclosed subject matter system and method include, a level of quality of the aligners and treatment is improved, because two (2) orthodontist's (i.e., a first, diagnosing orthodontist and a second, confirming orthodontist) agree on the diagnosis, the aligners are digitally designed by a highly trained orthodontist using the 3-D image of the mouth and teeth of the patient, a third orthodontist reviews and approves the aligners before they are sent to the patient, and the patient is regularly monitored, either: virtually, by using audio, digital, and video communication methods, documents, images, files, and physical molds; or, in-person, during treatment by the first, diagnosing orthodontist. As a result, better tooth position malocclusion correction outcomes are realized for the patient.

Other advantageous and new features include: 1) an at home kit for patients to take their own bite registrations that, once completed by the patient, are sent to be scanned to create a digital 3D mold of the teeth and mouth of the patient, which is then examined to determine whether the patient has correctable tooth position malocclusions; 2) send patient to Dental Scan Center for an Intraoral scan and create a direct digital mold; 3) use traditional PVS & send for scanning to create an indirect digital mold; and 4) other mouth and tooth digital scanning equipment. Still further advantageous features of the presently disclosed subject matter are that a patient be 18 years or older, because the patient's jaw and mouth have generally stopped growing by the time the patient is 18 years old, so this reduces the chances of future tooth movement, which increases the chances of a successful correction of the patient's tooth position malocclusion. A further benefit, is that, while the current Medical Standard of dental care only calls for a full mouth series (FMS) be done every 3 years and bitewing X-rays every year, the present system and method, during the active treatment phase, utilizes probing & bitewing X-rays every 12 months and a FMS every 24 months. This additional level of care helps to ensure a successful treatment outcome for the patient's tooth position malocclusion, but can also improve the patient's general dental health, due to the increased level of scrutiny of the mouth and teeth of the patient.

To address the above-described problem, embodiments of the subject network-based patient tooth malocclusion diagnosis and treatment method and system were developed to collect, convert, consolidate, and share patient information from various dental professionals and dental service and appliance providers in at least one standardized format, store it in centralized network-based storage devices, and provide access to authorized dental professionals, suppliers/service providers, and patients to the information. This will enable accurate diagnosis and treatment of each patient's unique and specific malocclusion condition. The method and system provides a graphical user interface (GUI) through a content server platform, which can be hardware or a combination of both hardware and software and can be integrated with or independent from the content server platform. A user, for example, but not limited to, a dental professional (i.e., a dentist or an orthodontist), is given a user-specific level of access to the content server platform through the GUI to enter, view or update information about a patient's medical condition using the user's own local device (e.g., but not limited to, a personal computer, laptop, tablet, or wireless handheld device). When the user wants to update the patient's records, the user can input the update via the user's chosen device directly into the content server platform base on the user's user-specific level of access. Whenever the patient information is updated, it is stored in a collection of patient medical records on one or more of the network-based storage devices. After the updated information about the patient's condition has been stored in the collection of patient medical records, the content server, which is connected to the network-based storage devices, automatically generates a message containing the updated information about the patient's condition. This message can be selectively transmitted over the computer network to all dental professionals, dental service, and appliance providers that have authorized access to and need to know the patient's updated information via the content server platform. This ensures that each of the necessary dental professionals and dental service and appliance providers is always given immediate notice and access to changes so they can readily adapt their own medical diagnostic and treatment strategy in accordance with other providers' actions and provided information. The message can be in the form of an email message, a text message, or other type of message known in the art.

In various embodiments of the presently disclosed subject matter, a method for treating a patient with removable teeth aligners, wherein the patient is suffering from tooth position abnormalities, includes determining whether the patient has a correctable tooth position abnormality or an uncorrectable tooth position abnormality by: obtaining or having obtained a mold (for example, but not limited to, a traditional dental mold) or a 3D image of the mouth and teeth of the patient; and performing or having performed an analysis of that mold or image of the mouth and teeth of the patient by a licensed dental professional (for example, but not limited to, a licensed dentist or a licensed orthodontist) to determine whether the patient qualifies with a healthy dentition and has a correctable tooth position abnormality. If the licensed dental professional determines the patient has a healthy dental status and has the correctable tooth position abnormality, verifying or having verified by an orthodontist the licensed dental professional's determination that the patient has the correctable tooth position abnormality. If the orthodontist verifies the licensed dental professional's determination that the patient has the correctable tooth position abnormality, then, if the patient's correctable tooth position abnormality is determined to be a minor correctable tooth position abnormality, providing a minor plurality of differently configured, removable teeth aligners based on the mold or image of the mouth and teeth of the patient, which are each to be administered to the teeth of the patient for a first predetermined length of time, for example, a predetermined number of days or weeks, and for a predetermined number of hours per day; or, if the patient's correctable tooth position abnormality is determined to be a major correctable tooth position abnormality, then providing a major plurality of differently configured, removable teeth aligners based on the mold of the mouth and teeth of the patient, which are each to be administered to the teeth of the patient for a second predetermined length of time, for example, a predetermined number of days or weeks, and for a predetermined number of hours per day. It may be determined that the patient's condition is too complex to use aligners alone, but may qualify for wire therapy, or a hybrid combination of aligners and wire therapy, which treatment is described below. Finally, if it is determined that the patient has the correctable tooth position abnormality, then upon completion of the administering of each of either the minor plurality of differently configured, removable teeth aligners, or the major plurality of differently configured, removable teeth aligners, providing a final removable teeth aligner based at least partially on the mold of the mouth and teeth of the patient and which is to be administered to the teeth of the patient for a third predetermined amount of time, for example, but not limited to, at least 12 hours per day and lifetime wear.

In various embodiments of the presently disclosed subject matter, a method for treating a patient with removable teeth aligners, wherein the patient is suffering from tooth position abnormalities, the method including: determining whether the patient has a correctable tooth position abnormality by: obtaining or having obtained a digital 3-dimensional mold of the mouth and teeth of the patient; and performing or having performed an analysis of the digital 3-dimensional mold of the mouth and teeth of the patient by a first licensed dental professional to determine whether the patient has a correctable tooth position abnormality or if it is an uncorrectable tooth position abnormality. If the first licensed dental professional determines the patient has the correctable tooth position abnormality, verifying or having verified by a second licensed dental professional the first licensed dental professional's determination that the patient has the correctable tooth position abnormality. If the second licensed dental professional verifies the first licensed dental professional's determination that the patient has the correctable tooth position abnormality, then: if the patient's correctable tooth position abnormality is determined to be a minor abnormality, providing a plurality of minor differently configured, removable teeth aligners based on the digital 3-dimensional mold of the mouth and teeth of the patient, which are each to be administered to the teeth of the patient for one to two weeks and for at least 20 hours/day, and if the patient's correctable tooth position abnormality is determined to be a major abnormality, then providing a plurality of major differently configured, removable teeth aligners based on the digital 3-dimensional mold of the mouth and teeth of the patient, which are each to be administered to the teeth of the patient for one to two weeks and for at least 20 hours/day. The plurality of minor differently configured, removable teeth aligners and the plurality of major differently configured, removable teeth aligners are administered to the teeth of the patient in a predetermined order. If it is determined that the patient has the correctable tooth position abnormality, then upon completion of the administering of either the plurality of minor differently configured, removable teeth aligners or the plurality of major differently configured, removable teeth aligners, providing a final removable teeth aligner based at least partially on the digital 3-dimensional mold of the mouth and teeth of the patient, which is to be administered to the teeth of the patient for at least 12 hours/day and lifetime wear.

In various embodiments of the presently disclosed subject matter, a method for treating a patient with removable teeth aligners, wherein the patient is suffering from tooth position abnormalities, the method comprising: a) storing information in at least one standardized format about a patient's tooth position malocclusion condition through a graphical user interface in one or more network-based non-transitory storage devices having a collection of dental records stored thereon, the information including three-dimensional (3-D) images of the mouth and teeth of the patient; b) providing a user-specific level of access to multiple users over a network, so any one of the multiple users can review and update the information about the patient's tooth position malocclusion condition in the collection of dental records in real time through the graphical user interface based on each user's user-specific level of access, wherein the updated information from at least one of the multiple users is provided in a non-standardized format; c) converting, by a content server, the non-standardized format updated information into updated information in the standardized format; d) storing the standardized format updated information about the patient's tooth position malocclusion condition in the collection of dental records in the standardized format; e) storing, in the collection of dental records, an initial diagnosis of the patient's tooth position malocclusion condition being correctable from a first dental professional user; f) storing, in the collection of dental records, a confirmatory diagnosis of the patient's tooth position malocclusion condition being correctable from an orthodontist user; g) storing, in the collection of dental records, digital designs for a set of progressive aligners based on the 3-D images of the mouth and teeth of the patient that are configured to progressively correct the patient's tooth position malocclusion condition; h) sending an order message with the designs for the set of progressive aligners based on the 3-D images of the mouth and teeth of the patient to an aligner manufacturer; i) receiving a completed order message that the aligners are complete and have been shipped to an approving orthodontist for review and approval; j) receiving an approval message from the approving orthodontist; k) automatically generating a ready message containing the updated information about the approved aligners by the content server; and l) transmitting the ready message to at least the dental professional, patient, and aligner manufacturer users over the computer network in real time, so that each user has immediate access to up-to-date patient dental information.

FIG. 1 is a block system diagram showing a configuration of a Virtual Reality Orthodontics (VRO) system illustrating the system components and communication paths there between, in accordance with various embodiments of the disclosed subject matter. In the exemplary embodiment in FIG. 1, a system 100 includes an integrated patient VRO system 110 that includes a VRO platform 111 connected to a practice management system platform 112 via an internal secure communication connection 113, or, alternatively, the practice management system platform 112 can be external to the VRO system 110 and connected to and in communication with the VRO platform 111 through an external communication network 120, for example, but not limited to, Internet 120, via one or more VRO platform secure Internet communications connections 124. While the embodiment of the VRO system 110 and the VRO platform 111 in FIG. 1 is shown as one system, in other embodiments, the functionality of the VRO system 110 can be implemented in one or more distributed systems. In FIG. 1, the VRO platform 111 can include a processor 114 that is communicatively connected to a bus 115 or other communication system, is for processing information and can be a one of many types of general purpose or specific purpose processors, as well as an application-specific integrated circuit ("ASIC") processor. The VRO platform 111 further includes a memory 116 for storing data, information and processor-executable instructions such as for a graphical user interface 117 and an operating system 119, as well as data in a patient dental record database 118. Memory 116 is communicatively connected to bus 115, which is also communicatively connected to a communication device 123, which is configured to enable communications with internal VRO system 110 components and with Internet 120 via the one or more VRO platform secure Internet communications connections 121. Communication device 123 can include one or more network interface (NIC) cards for a wired network connection (e.g., but not limited to, a cable, an Ethernet, or a fiber optic connection) and a wireless network connection (e.g., but not limited to, a Wi-Fi, a cellular, an infrared, and a radio connection). The practice management system platform 112 can be implemented and executed within VRO platform 111 as well as on a separate, connected computing system, similar to that described above for VRO platform 111 and including similar components (for example, but not limited to, a second processor, a second bus, a second memory, a second communications device, etc.).

VRO platform 111, in FIG. 1, further includes a system workstation 122 communicatively connected to bus 115 and can be used primarily for administrative management of VRO system 110 and VRO platform 111. Although not separately shown, system workstation 122 can include its own processor, bus, memory, communication device, non-volatile storage system, and programs for accessing and controlling VRO system 110 and VRO platform 111, as well as peripheral devices like a keyboard, a mouse, and a display.

In FIG. 1, memory 116 includes processor-executable code for a graphical user interface (GUI) 117 and an operating system 119, as well as a patient dental record database 118. Integrated patient platform 110, as well as VRO platform 111 and practice management system platform 112, can be accessed through GUI 117 by at least one teeth imager and teeth mold maker 125 (for example, but not limited to, a smile center 125), at least one aligner manufacturer 127, multiple patients 130-1-130-N, multiple dental professionals 140-1-140-M, multiple VRO dental professionals 150, and one or more finance companies 160 (both the multiple VRO dental professionals 150, and one or more finance companies 160 are shown here as single components for convenience). This access can be via one or more secure direct communications connections or secure Internet communications connections. For example, the at least one teeth imager and teeth mold maker 125 and the at least one aligner manufacturer 127 can communicate with VRO platform 111 via secure direct communications connections 126 and 129, respectively. Although not shown, the at least one teeth imager and teeth mold maker 125 and the at least one aligner manufacturer 127 can also communicate with VRO platform 111 via secure Internet 120 communications connections. VRO platform 111 can communicate over the Internet via the one or more VRO platform secure Internet communications connections 121; and the practice management system platform 112 can communicate over the Internet 120 via one or more diagnostic, design, and patient monitoring platform secure Internet communications connections 124. Likewise, each of the multiple patients 130-1-130-N can communicate through the Internet via secure communications connection 131-1-131-N, respectively, as well as being able to communicate directly with their respective dental professional 140-1-140-M via secure direct communications connections, for example, a first patient 1 130-1 can communicate with a last dental professional 1 140-1 via a secure direct communications connection 132. Similarly, a last patient N 130-N can communicate with a last dental professional 1 140-M via a secure direct communications connection 133. Of course, each of the multiple patients 130-1-130-N can communicate directly with each of the multiple dental professionals 140-1-140-M and multiple VRO dental professionals 150 via other secure direct communications connections (not shown). Each of the multiple dental professionals 140-1-140-M can communicate through the Internet via secure communications connections 141-1-141-M, respectively. In addition, each of the multiple VRO dental professionals 150 can communicate with the other entities in the system 100 over the Internet via one or more secure VRO dental professionals communications connections 151.

An exemplary, but not limiting, example of one method of obtaining and treating the patient 130-1 using the system 100 of FIG. 1 is through, for example, but not limited to, recruiting the patient 130-1 using direct marketing efforts and entering the patient 130-1 into VRO system 110 through VRO platform 111 without a referral from a treating doctor, for example, dental professional 140-1. In this instance, patient 130-1, through VRO platform 111, registers and creates a patient dental record in a patient dental record database 118 in VRO system 110, and then enters their dental information and photos of their mouth and teeth into their patient dental record in the patient dental record database 118. The patient dental record database 118 is accessible using a secure, artificial intelligence (AI) system 128, for example, but not limited to, an existing system like SmileMate™ from Dental Monitoring. The AI system 128 can be implemented in a practice management system (PMS) platform 112 or can be a separate program that can be accessed through the PMS platform 112. After the patient 130-1 has entered their dental information and photos of their mouth and teeth, a first VRO orthodontist 151-1 from multiple VRO dental professionals 150, through VRO system 110 and/or the PMS platform 112, accesses and uses the secure, AI system 128 to determine whether the patient qualifies for treatment using a patient dental report with a proposed length of treatment and cost generated by the secure, AI system 128. If the patient qualifies for treatment, the first VRO orthodontist 151-1, through VRO system 110, sends a message to the patient 130-1 to go to an affiliated dental professional 140-1 or an affiliated dental scan center 125 (who is paid by VRO) to have an image of the patient's 130-1 mouth made. The first VRO orthodontist 151-1 also sends a request message, i.e., a work order, through VRO system 110 to the affiliated dental professional 140-1 or the affiliated dental scan center 125 to let them know the patient 130-1 will be coming and to obtain the patient's initial dental record information, including, but not limited to, digital 3-dimensional molds of the patient's teeth and mouth. Once the patient's initial dental record information is collected, the affiliated dental professional 140-1 or the affiliated dental scan center 125 sends the patient's initial dental record information to VRO orthodontist 151-1, through VRO system 110, where it is stored in the patient dental record in the central database 118 in the memory of the integrated platform and is connected to and accessible by the practice management system platform 112, for example, but not limited to, an existing system like GreyFinch.from Greyfinch, LLC. The patient 130-1, through VRO system 110 via the GUI 117, is also able to set up an account with a payment and loan processing provider, for example, but not limited to, GreenSky, LLC. VRO orthodontist 151-1, using a 3-dimensional software system, for example, but not limited to, SureSmile from Dentsply Sirona, that is accessed through VRO system 110 diagnoses, creates a prescribed treatment plan, and creates a digital design for a set of progressive aligners to treat the patient's tooth position malocclusions. Once finalized, VRO orthodontist 151-1 sends a patient case file with the diagnosis, the prescribed treatment plan, and the digital design for the patient's set of progressive aligners through VRO system 110 to a second VRO orthodontist 150-2 for quality control to review and confirm VRO orthodontist's 151-1 diagnosis and prescribed treatment plan. If approved, the second VRO orthodontist 150-2 sends the patient case file, through VRO system 110, to a state evaluator 170 for final approval. The state evaluator 170 is a licensed and highly trained dental professional, for example, but not limited to, an orthodontist with training and extensive experience in the use of 3-D digital dental diagnostic, treatment planning, and orthodontic appliance and aligner design and manufacturing. The state evaluator can be a non-VRO orthodontist as well as one or more of VRO orthodontists.

Once VRO orthodontist 151-1 receives the final approval back from the state evaluator 170, through VRO system 110, VRO orthodontist 151-1 sends an order, also through VRO system 110, to an aligner manufacturer 127 to manufacture the patient's set of progressive aligners. Once completed, the aligner manufacturer 127 sends a message, through VRO system 110, to VRO orthodontist 151-1 and an aligner approving orthodontist, who can be, for example, but not limited to, the first VRO orthodontist 151-1 or the second VRO orthodontist 151-2 that the aligners are ready and ships the patient's set of progressive aligners to the aligner approving orthodontist 150-1, 150-2 to be reviewed and approved before being sent to the patient 130-1. In addition, the aligner approving orthodontist can be another qualified VRO orthodontist 150-3-150-$n$ or a qualified non-VRO orthodontist (not shown). As seen in FIG. 1, the aligner approving orthodontist is one of the multiple VRO dental professionals 150, for example, either the first VRO orthodontist 150-1 or the second VRO orthodontist 150-2. If the aligners are approved, the aligner approving orthodontist 150-1, 150-2 sends a message that the aligners are ready to the patient 130-1, the aligner manufacturer 127 and the first VRO orthodontist 150-1 (if not the aligner approving orthodontist), through VRO system 110, and ships the patient's set of progressive aligners along with written, photo, and video instructions on how to insert and wear the patient's set of progressive aligners along with an AI monitoring device directly to the patient 130-1. The AI monitoring device can include, for example, but is not limited to, a personal mobile phone, tablet, digital camera, and any other dental scanner, If the aligners are not approved, the aligners are returned to the aligner manufacturer 127 with instructions on what needs to be corrected and messages about the needed corrections are send to the first VRO orthodontist 150-1 and the aligner manufacturer 127, through VRO system 110. Once the corrections have been made the aligner manufacturer 127 sends a new message, through VRO system 110, to the first VRO orthodontist 150-1 and the aligner approving orthodontist 150-1, 150-2 that the corrected aligners are ready and then sends the patient's corrected set of progressive aligners to an approving orthodontist to be reviewed and approved before being sent to the patient 130-1. If the corrected aligners are approved, the aligner approving orthodontist 150-1, 150-2 sends a message that the aligners are ready to the patient 130-1, the aligner manufacturer 127, and the first VRO orthodontist 150-1, through VRO system 110, and ships the patient's set of progressive aligners along with written, photo, and video instructions on how to insert and wear the patient's set of progressive aligners and the above-described AI monitoring device directly to the patient 130-1.

During an active treatment phase where the patient 130-1 is wearing the prescribed aligners for a prescribed time each day, the patient 130-1 can be monitored for progression analysis by the first VRO orthodontist 150-1, through VRO system 110. If needed, the patient 130-1 can be directed to the state evaluator 170 for a physical or virtual visit for progression analysis. Once the prescribed treatment plan is completed, the patient 130-1 will be shipped one or more retention devices with written, photo, and video instructions, i.e., a final aligner that is designed to maintain a final tooth position achieved by the prescribed treatment plan that is commonly referred to as a retainer. The one or more retention devices were designed as part of the initial treatment plan, but, they can either be produced with the patient's set of prescribed aligners or can be produced after the prescribed treatment plan is completed. In this way it is possible for the first VRO orthodontist 150-1 to adjust the digital design of the one or more retention devices, if the patient's actual final tooth position varies from the prescribed treatment plan.

Alternatively, if the patient 130-1 already has a doctor 140-1 (for example, a General Practice dentist 140-M who is not trained or equipped to perform some or all of the aligner treatment, one of the affiliated dental professionals 140-M, or the affiliated dental scan centers 125), for a fee, the doctor can place the patient into VRO system 110 and use VRO platform and method of treatment for the patient. In yet another alternative, doctors can refer their patients to the first VRO orthodontist 150-1 to handle the entire treatment process, as described above, and the referring doctor can receive compensation for the referral, but is still able to monitor the patient's progress during the treatment process. This can positively affect the patient's ultimate treatment and the referring doctor's income with a minimal time and out-of-pocket expense commitment, because it can free up the referring doctor's in-office resources and time to see other patients with conditions in line with the referring doctor's practice.

Additional advantages of the presently disclosed subject matter system and method include, a level of quality of the aligners and treatment is improved, because two (2) VRO orthodontist's (i.e., a first, diagnosing orthodontist and a second, confirming orthodontist) agree on the diagnosis, a State evaluator reviews and approves the plan, the aligners are digitally designed by a highly trained orthodontist using the 3-D image of the mouth and teeth of the patient, a third orthodontist, also referred to as an approving orthodontist, reviews and approves the aligners before they are sent to the patient, and the patient is regularly monitored, either virtually or in-person, during treatment by the first, diagnosing orthodontist. As a result, not only can better tooth position malocclusion correction outcomes be realized for the patient, but also patients that might not normally have access to receive this level of treatment now will be able to receive treatment.

Figure 2:
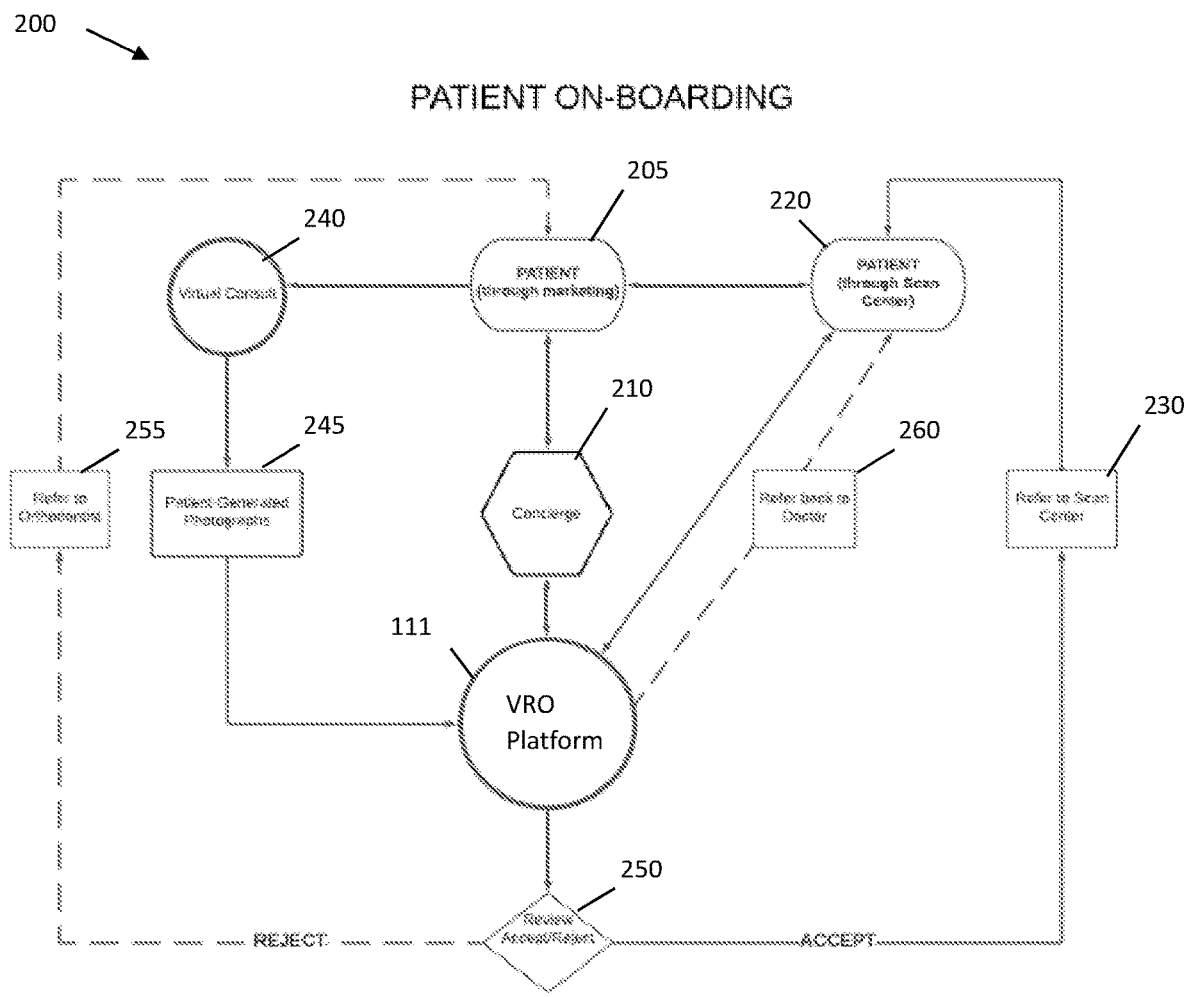
FIG. 2. is a flow diagram of an overview of a patient onboarding process for a method of diagnosing and treating a patient with a correctable tooth malocclusion, in accordance with various embodiments of the disclosed subject matter.

FIG. 2 is a flow diagram of an overview of a patient onboarding process 200 for a method of diagnosing and treating a patient 205 with a correctable tooth malocclusion, in accordance with various embodiments of the disclosed subject matter. In FIG. 2, the patient 205 can enter the patient onboarding process 200 as a result of direct marketing by VRO dental professionals 150, by the other dental professionals 140-1-140-M, or through a dental scan center 230. If the patient 205 is brought in by VRO dental professionals 150, generally the patient 205 first goes through a concierge 210, for example, but not limited to, a VRO concierge 210 to, among other things, get the patient 205 registered in VRO platform 111, explain the process, schedule appointments, arrange financing, and answer questions. If the patient 205 is brought in through a dental scan center 230, which generally happens after the patient 205 was sent to the dental scan center 230 by the patient's dental professional, the patient 205 can be brought directly into VRO platform 111 by the dental scan center 230 or, alternatively, through the concierge 210. Once the patient 205 is in VRO platform 111, an initial virtual consult 240 is held between the patient 205 and one or more of VRO dental professionals 150 to determine whether the patient 205 is a potential candidate for treatment and, if the patient 205 is a candidate, the patient 205 generates photographs 245 of their mouth and teeth and submits them to VRO platform 111 for review and evaluation 250 by VRO dental professionals 150. If the review and evaluation 250 results in the patient 205 being accepted, the patient 205 is referred to the dental scan center 230 to have a 3-dimensional (3-D) scan done of the patient's teeth and mouth to create a full size, 3-D model of the patient's teeth and mouth. It is the full size, 3-D model of the patient's teeth and mouth that is used to design and manufacture the teeth aligners to correct the patient's 205 teeth malocclusions. If the review and evaluation 250 results in the patient 205 being rejected, the patient is referred 255 to an orthodontist for treatment using traditional braces and wires.

In FIG. 2, if the patient 205 is accepted after the review and evaluation 250 and was brought in through the dental scan center 230, the patient 205 can be referred back to the dental scan center 230 for monitoring during the treatment. In FIG. 2, if the patient 205 is accepted after the review and evaluation 250 and was brought in through to the patient's 205 dental professional (see, FIG. 1, 140-1-140-N), the patient 205 can be referred back to the patient's 205 dental professional for monitoring during the treatment.

Figure 3:
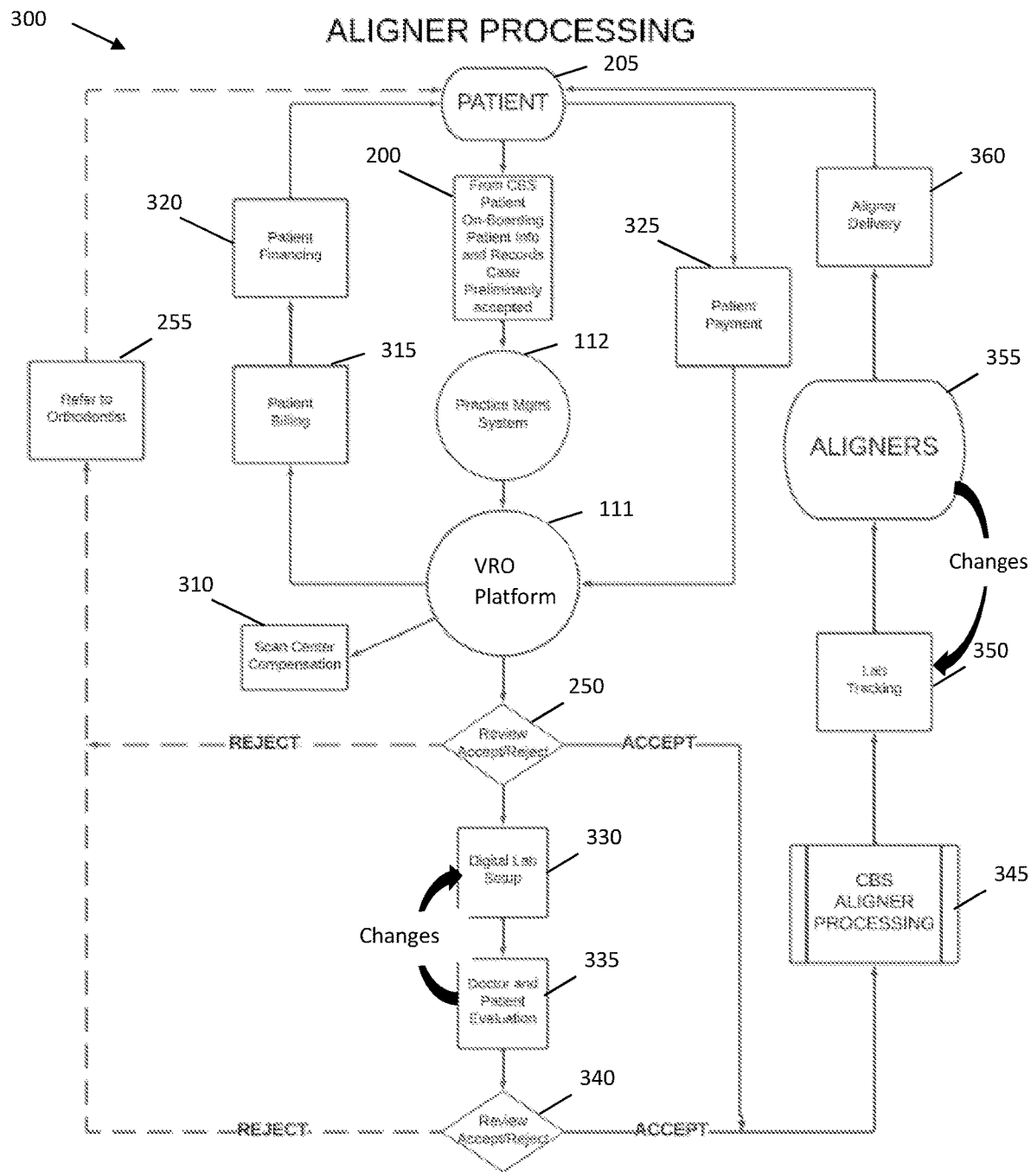
FIG. 3 is a flow diagram of an overview of a teeth aligner process for use in the method of diagnosing and treating the patient with the correctable tooth malocclusion, in accordance with various embodiments of the disclosed subject matter.

FIG. 3 is a flow diagram of an overview of a teeth aligner process 300 for use in the method of diagnosing and treating the patient 205 with the correctable tooth malocclusion, in accordance with various embodiments of the disclosed subject matter. In FIG. 3, the patient onboarding process 200 of FIG. 2 has been performed and the patient 205 information and records are in VRO platform 111 and can be accessed through the practice management system platform 112 that is in communication with VRO platform 111. VRO platform 111 can coordinate and control making payments to the dental scan centers 310, preparing and sending patient bills 315, and coordinating, obtaining, and controlling third party financing 320 of the patient's 205 treatment. In addition, VRO platform 111 can receive and account for patient payments 325.

In FIG. 3, VRO platform 111 provides the patient 205 information for review and evaluation 250 by VRO dental professional 150. If the review and evaluation 250 results in the patient 205 being accepted, the patient is sent to have a digital lab 330 create the digital model of the mouth and teeth of the patient. Following the digital lab 330 creation of virtual designs for one or more aligners and a final retainer based on the 3-D digital model of the mouth and teeth of the patient, VRO dental professional 150 and the patient 205 review and evaluate 335 the virtual designs for one or more aligners and the final retainer virtually through VRO platform 111. If VRO dental professional 150 and the patient 205 believe changes need to made to the virtual designs for one or more aligners and the final retainer, then the needed changes are sent back to the digital lab 330 to implement the changes and return for final review by VRO dental professional 150 and the patient 205. If the review and evaluation 335 results in VRO dental professional 150 and the patient 205 both accepting 340 the virtual designs for the one or more aligners and the final retainer, the virtual designs for the one or more aligners and the final retainer are then processed 345 by VRO dental professional 150 and sent to an aligner manufacturing lab 350 to produce the actual one or more aligners and final retainer from the virtual designs. As noted previously, the one or more aligners and the final retainer are unique to each patient 205 and their specific teeth malocclusions. After the aligner manufacturing lab 350 produces the one or more aligners and the final retainer, they are sent for review and approval 355 by VRO dental professional 150 or another VRO dental professional 150. In general, this review is a physical review to ensure the quality and correctness of the one or more aligners and the final retainer, but it can also be performed virtually through VRO platform 111, either manually or using Artificial Intelligence (AI) software. The virtual review can be accomplished by having the aligner manufacturer send digital scans of each of the one or more aligners and the final retainer, which can be compared against the original virtual designs for the one or more aligners and the final retainer that were created by VRO dental professional 150. If approved, the one or more aligners and the final retainer are sent to the patient 205. If corrections are needed, the one or more aligners and the final retainer are sent 356 back to the aligner manufacturing lab 350 for the corrections and return for another review and approval 355 by VRO dental professional 150. Once approved, the one or more aligners and the final retainer are sent 360 to the patient 205 to begin treatment of the patient 205.

In FIG. 3, if the review and evaluation 335 results in either the doctor or the patient 205 rejecting 340 the original virtual designs of the aligners for the patient's 205 teeth, then the patient 205 is referred out of VRO platform 111 to a regular, "brick and mortar" orthodontist 255 for traditional orthodontic treatment.

Figure 4:
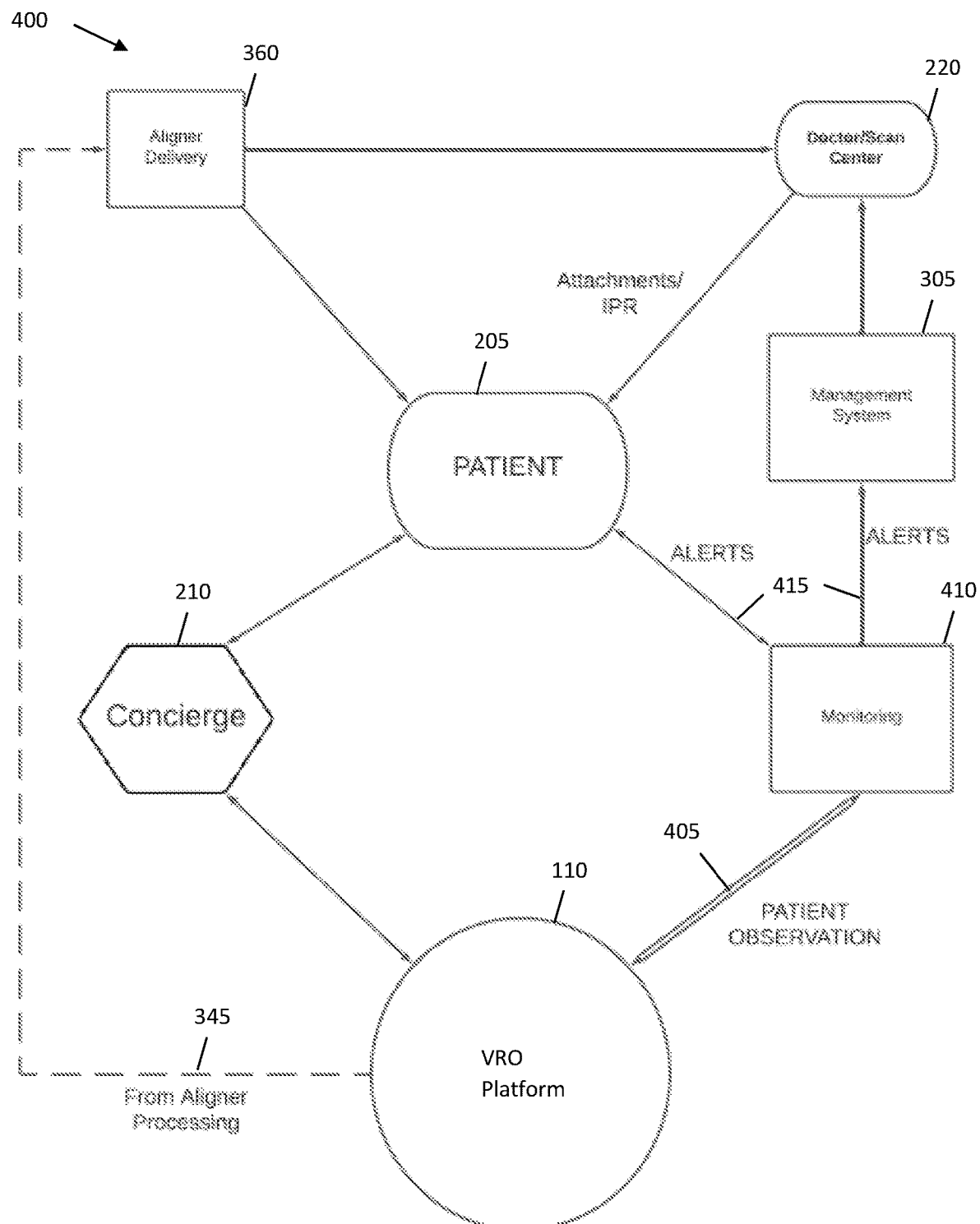
FIG. 4 is a system flow diagram of the patient interaction, i.e., experience, with the VRO system and method, in accordance with various embodiments of the disclosed subject matter.

FIG. 4 is a system flow diagram of the patient 205 interaction, i.e., experience, with VRO system 110 and method, in accordance with various embodiments of the disclosed subject matter. In FIG. 4, the patient 205 experience with VRO system 110 and method using VRO platform 111 from on-boarding through VRO concierge 210, obtaining the digital model of their mouth and teeth, being diagnosed as a viable candidate and accepted for treatment, accepting 340 the one or more aligners and the final retainer, the aligner provision process, to actually being treated and virtually monitored by VRO dental professional 150, the scan center doctor, and/or the patient's referring physician through VRO platform 111.

In FIG. 4, during treatment, the patient 205 is regularly observed 405 and monitored 410 by VRO dental professional 150 through VRO platform 111, which permits direct visual interaction and communication between the patient 205 and VRO dental professional 150. If a problem or an issue is diagnosed by VRO dental professional 150, an alert 415 can be sent to the patient. In addition, if the patient 205 was initially referred by an outside dental professional or from a doctor at the scan center 220, the alerts 415 can be sent to them at the same time as the alerts 415 are sent to the patient 205.

Figure 5:
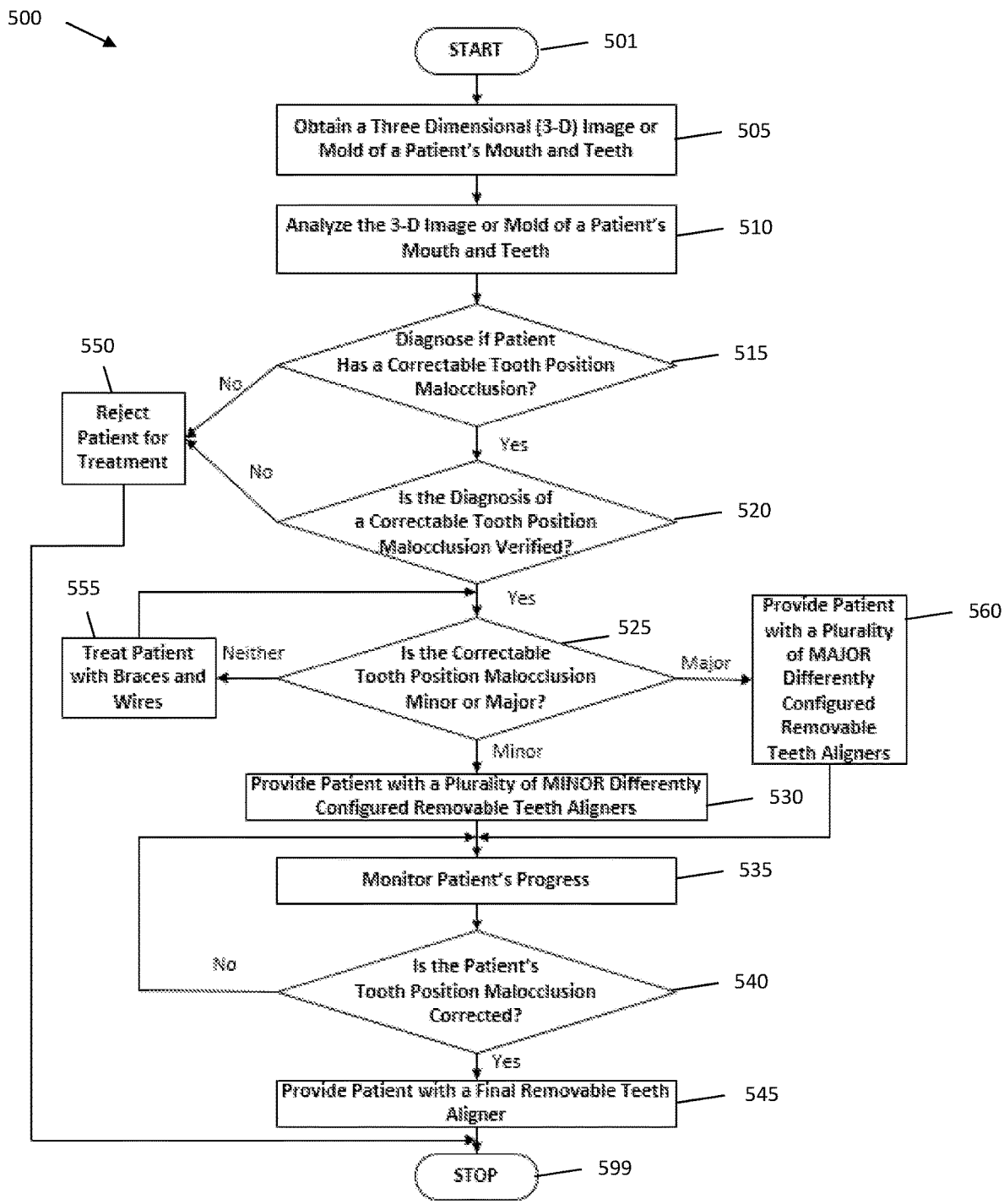
FIG. 5 is a flow chart diagram of a patient diagnostic and treatment process, in accordance with various embodiments of the disclosed subject matter.

FIG. 5 is the flow chart diagram of a patient diagnostic and treatment process, in accordance with various embodiments of the disclosed subject matter. In FIG. 5, a patient diagnostic and treatment process 500 starts 501 and a three dimensional (3-D) image or mold of the mouth and teeth of the patient is obtained 505 and then analyzed 510 by a first dental professional, i.e., a first dentist or a first orthodontist, to determine 515 whether the patient 205 has a good, i.e., healthy, dentition and a correctable tooth position malocclusion. If the patient 205 is determined 515 to have the good dentition and the correctable tooth position malocclusion, then the diagnosis is reviewed by a second dental professional, i.e., a second dentist or a second orthodontist, to verify 520 whether the diagnosis of the good dentition and the correctable tooth position malocclusion is correct. If verified 520, then if the tooth position malocclusion is determined 525 to be a minor malocclusion, then the patient is provided 530 with a plurality of minor differently configured removable teeth aligners, each of which the patient 205 is to where for a predetermined number of days or weeks and for a predetermined number of hours each day. The predetermined number of days or weeks and the predetermined number of hours each day are determined and prescribed by either the first or second dental professional. For example, in some embodiments of the presently disclosed subject matter, the predetermined number of days or weeks can be from 1 to 4 weeks and the predetermined number of hours each day can be from 12 to 20 hours per day. In a specific embodiment, the predetermined number of days or weeks can be from 1 to 2 weeks and the predetermined number of hours each day can be 20 hours per day.

In FIG. 5, if verified 520, then if the tooth position malocclusion is determined 525 to be a major malocclusion, then the patient is provided 530 with a plurality of major differently configured removable teeth aligners, each of which the patient 205 is to wear for a predetermined number of days or weeks and for a predetermined number of hours each day. The predetermined number of days or weeks and the predetermined number of hours each day are determined and prescribed by either the first or second dental professional. For example, in some embodiments of the presently disclosed subject matter, the predetermined number of days or weeks can be from 1 to 4 weeks and the predetermined number of hours each day can be from 12 to 20 hours per day. In a specific embodiment, the predetermined number of days or weeks can be from 1 to 2 weeks and the predetermined number of hours each day can be 20 hours per day.

Regardless, in FIG. 5, if the patient 205 is provided with the plurality of minor differently configured removable teeth aligners or the plurality of major differently configured removable teeth aligners, the patient's 205 progress is monitored 535 by one or both of the first dental professional and the second dental professional. After the prescribed course of treatment, the patient's 205 mouth and teeth are examined to determine 540 if the desired correction of the patient's 205 malocclusion has been obtained. If the desired correction of the patient's 205 malocclusion has been obtained, then the patient 205 is provided with a final removable retainer, which the patient 205 is to wear for a predetermined number of weeks or years and for a predetermined number of hours each day. As with the two plurality of aligners, the predetermined number of weeks or years and the predetermined number of hours each day are determined and prescribed by either the first or second dental professional. For example, in some embodiments of the presently disclosed subject matter, the predetermined number of weeks or years can be from 1 year to the rest of the patient's lifetime and the predetermined number of hours each day can be from 8 to 16 hours per day. In a specific embodiment, the predetermined number of weeks or years can be from for the rest of the patient's lifetime and the predetermined number of hours each day can be 12 hours per day. After being provided with the retainer, the treatment process stops 599.

In FIG. 5, if the desired correction of the patient's 205 malocclusion has not been obtained, then the patient 205 loops back and continues treatment and monitoring 535 until the desired correction of the patient's 205 malocclusion has been obtained.

In FIG. 5, if verified 520, then if the tooth position malocclusion is determined 525 to be neither a minor nor a major malocclusion, but more than a major malocclusion, then the patient 205 can be provided with a hybrid treatment in which the patient 205 is first treated with traditional braces and wires until the tooth position malocclusion is determined 525 to be either a minor or a major malocclusion. Once the tooth position malocclusion is determined 525 to be either a minor or a major malocclusion after treatment with the braces and wires, then the patient is treated as described above based on the level of diagnosed malocclusion.

In FIG. 5, if the patient 205 is not diagnosed 515 with a correctable tooth position malocclusion or the diagnosis of a correctable tooth position malocclusion is not verified 520, then the patient 205 is rejected for treatment using the patient diagnostic and treatment process 500. The patient is generally referred for traditional braces and wires treatment, unless that treatment is not advisable for the patient 205.

Figure 6:
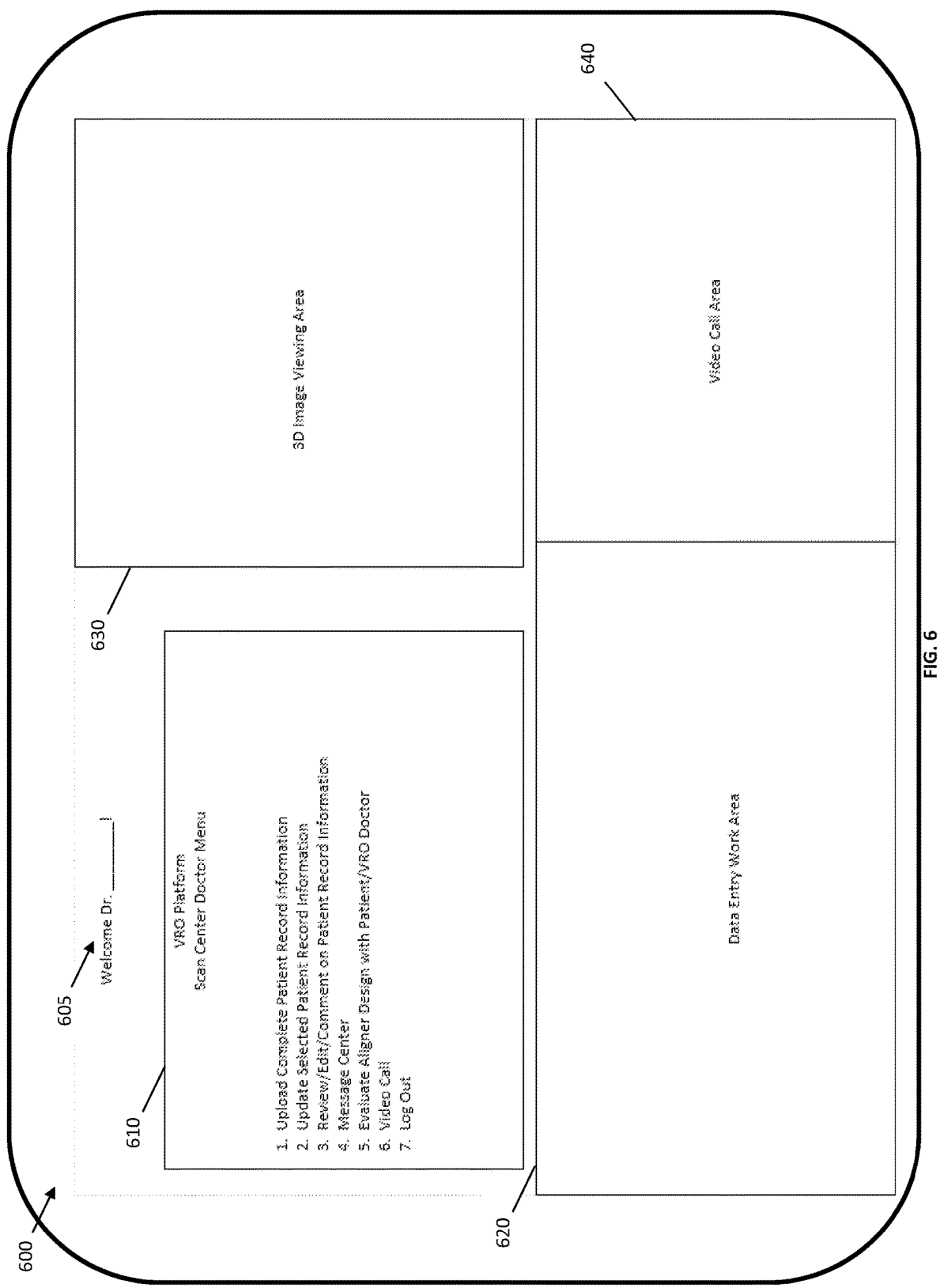
FIG. 6 is a block diagram showing a functional configuration of a graphical user interface (GUI) screen for a scan center doctor in a virtual reality orthodontics (VRO) platform system for diagnosing, prescribing, providing, and monitoring the use of clear aligners to correct tooth malocclusions, in accordance with various embodiments of the disclosed subject matter.

FIG. 6 is a block diagram showing a functional configuration of a graphical user interface (GUI) screen 600 for a scan center doctor in a virtual reality orthodontics (VRO) system 110 for diagnosing, prescribing, providing, and monitoring the use of clear aligners to correct tooth malocclusions, in accordance with various embodiments of the disclosed subject matter. In FIG. 6, the GUI for the scan center doctor's screen 600 can include a personalized welcome message 605 based on the individual user's login credentials, which also determines the configuration of a scan center doctor's menu section 610, a system access level, and to which patient information the scan center doctor can access in VRO platform 111. The listed menu options, which in FIG. 6 include, for example, but are not limited to, selections to: upload new patient information (see FIG. 10 for example details); update existing patient information; review/edit/comment on existing patient information; access a central message center through which all permitted other users can be contacted, evaluate aligner design; participate in video calls; and log out of in VRO platform 111. These options are merely illustrative of some of the possible options and in no way should be construed as limiting the options that can be implemented for the scan center doctor to use and access VRO platform 111.

In FIG. 6, also included in the GUI for the scan center doctor's screen 600 can be a scan center doctor's data entry work section 620 through which the scan center doctor can upload and access patient information to which the scan center doctor has the proper access level permission in VRO platform 111. For example, one or more of the menu options can be opened in the scan center doctor's data entry work section 620 and enable the scan center doctor to interact with and work in VRO platform 111. The GUI for the scan center doctor's screen 600 can also include a scan center doctor's image viewing section 630 through which the scan center doctor can view, evaluate, edit, and create images of patient information to which the scan center doctor has the proper access level permission in VRO platform 111. For example, the images can include, but are not limited to, a patient's x-rays, past dental records, 3-D images and/or molds of the patient's teeth and mouth, 3-D images of sets of aligners, and digital designs for the sets of aligners. In addition, for this embodiment, the GUI for the scan center doctor's screen 600 can also include a scan center doctor's communication section 640 through which the scan center doctor can communicate with the scan center doctor's patients as well as the other doctors, and suppliers who are working with the scan center doctor's individual patients in a single secure environment.

Alternatively, in FIG. 6, some or all of the functionality of the above-described scan center doctor's GUI sections 610, 620, 630, and 640 can be implemented in separate screens or windows as well as in popup window screens.

Figure 7:
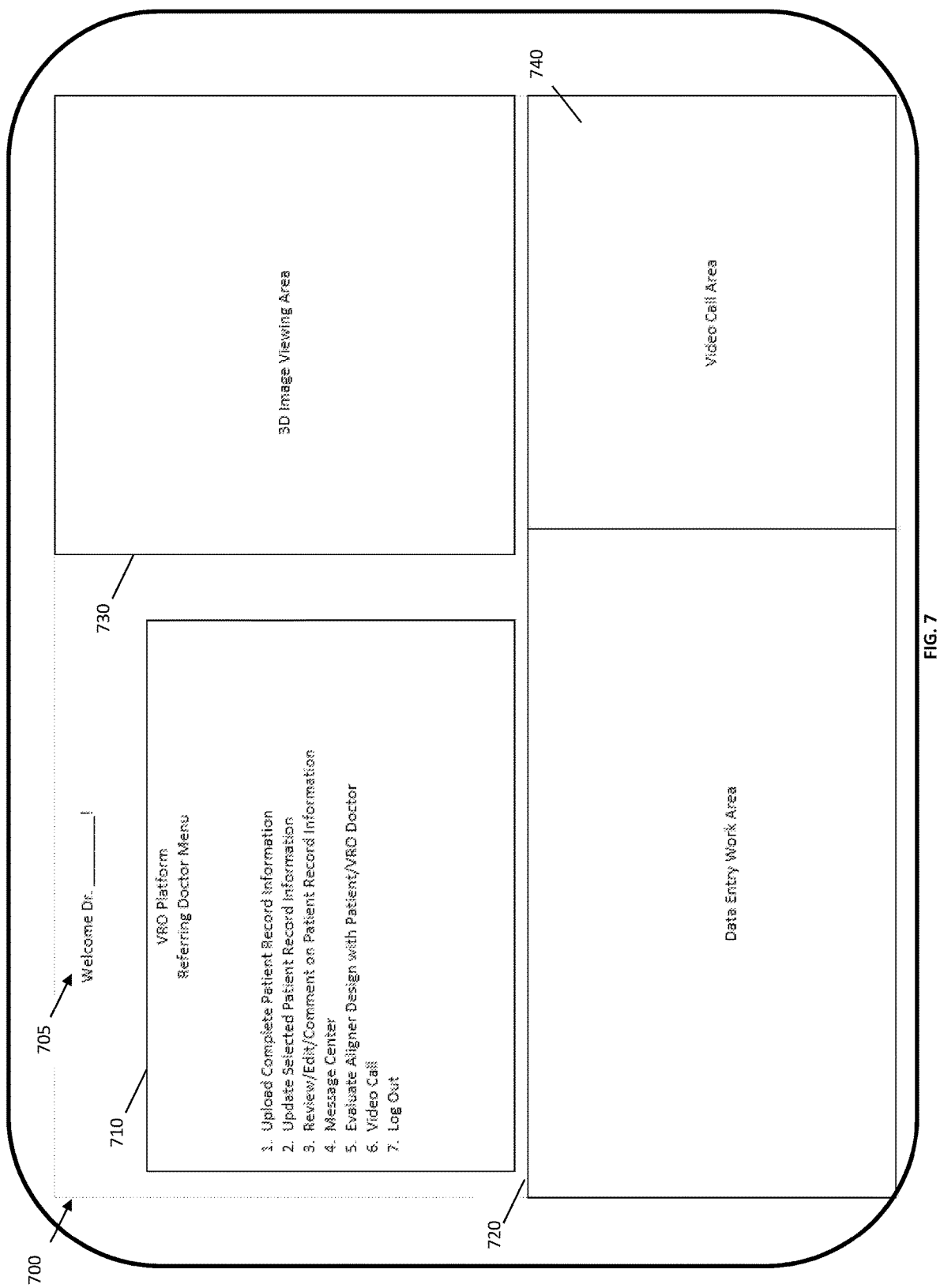
FIG. 7 is a block diagram showing a functional configuration of a GUI screen for a referring doctor from the VRO platform for diagnosing, prescribing, providing, and monitoring the use of clear aligners to correct tooth malocclusions, in accordance with various embodiments of the disclosed subject matter.

FIG. 7 is a block diagram showing a functional configuration of a GUI screen 700 for a referring doctor from VRO platform for diagnosing, prescribing, providing, and monitoring the use of clear aligners to correct tooth malocclusions, in accordance with various embodiments of the disclosed subject matter. In FIG. 7, the GUI for the referring doctor's screen 700 can include a personalized welcome message 705 based on the individual user's login credentials, which also determines the configuration of a referring doctor's menu section 710, a system access level, and to which patient information the referring doctor can access in VRO platform 111. The listed menu options, which in FIG. 7 include, for example, but are not limited to, selections to: upload new patient information; update existing patient information; review/edit/comment on existing patient information; access a central message center through which all permitted other users can be contacted, evaluate aligner design; participate in video calls; and log out of in VRO platform 111. These options are merely illustrative of some of the possible options and in no way should be construed as limiting the options that can be implemented for the referring doctor to use and access VRO platform 111.

In FIG. 7, also included in the GUI for the referring doctor's screen 700 can be a referring doctor's data entry work section 720 through which the referring doctor can upload and access patient information to which the referring doctor has the proper access level permission in VRO platform 111. For example, one or more of the menu options can be opened in the referring doctor's data entry work section 720 and enable the referring doctor to interact with and work in VRO platform 111. The GUI for the referring doctor's screen 700 can also include a referring doctor's image viewing section 730 through which the referring doctor can view, evaluate, edit, and create images of patient information to which the referring doctor has the proper access level permission in VRO platform 111. For example, the images can include, but are not limited to, a patient's x-rays, past dental records, 3-D images molds of the patient's teeth and mouth, 3-D images of aligners, and digital designs for the sets of aligners. In addition, for this embodiment, the GUI for the referring doctor's screen 700 can also include a referring doctor's communication section 740 through which the referring doctor can communicate with the referring doctor's patients as well as the other doctors, and suppliers who are working with the referring doctor's individual patients in the single secure environment.

Alternatively, in FIG. 7, some or all of the functionality of the above-described referring doctor's GUI sections 710, 720, 730, and 740 can be implemented in separate screens or windows as well as in popup window screens.

Figure 8:
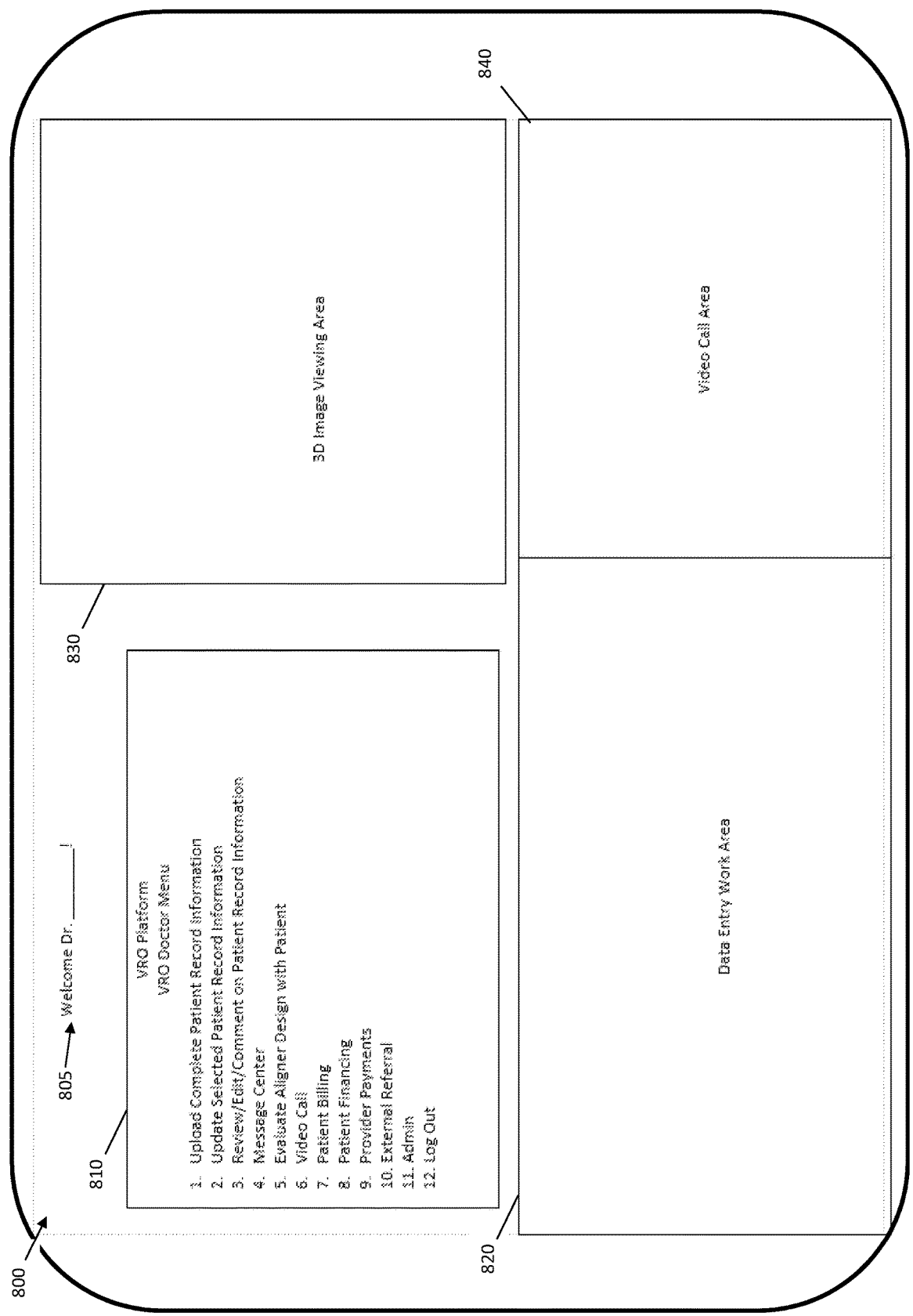
FIG. 8 is a block diagram showing a functional configuration of a GUI screen for a managing VRO doctor from the VRO platform for diagnosing, prescribing, providing, and monitoring the use of clear aligners to correct tooth malocclusions, in accordance with various embodiments of the disclosed subject matter.

FIG. 8 is a block diagram showing a functional configuration of a GUI screen 800 for a managing VRO doctor from VRO platform for diagnosing, prescribing, providing, and monitoring the use of clear aligners to correct tooth malocclusions, in accordance with various embodiments of the disclosed subject matter. In FIG. 8, the GUI screen 800 for the managing VRO doctor can include a personalized welcome message 805 based on the individual managing VRO doctor's login credentials, which also determines the configuration of a managing VRO doctor's menu section 810, a system access level, and to which patient information the managing VRO doctor can access in VRO platform 111. In general, the managing VRO doctor will have access to most, if not all, of the patients' information in VRO platform 111. The listed menu options, which in FIG. 8 include, for example, but are not limited to, selections to: upload new patient information; update existing patient information; review/edit/comment on existing patient information; access a central message center through which all permitted other users can be contacted, evaluate aligner design; participate in video calls; do patient billing; participate in the patient financing process; make payments to providers, which can include the referring and scan center doctors as well as the product providers; make external referrals of patients that do not qualify for treatment; perform administrative task on VRO platform 111; and log out of in VRO platform 111. These options are merely illustrative of some of the possible options and in no way should be construed as limiting the options that can be implemented for the managing VRO doctor to use and access VRO platform 111.

In FIG. 8, also included in the GUI for the managing VRO doctor's screen 800 can be a managing VRO doctor's data entry work section 820 through which the managing VRO doctor can upload and access patient information to which the managing VRO doctor has the proper access level permission in VRO platform 111. For example, one or more of the menu options can be opened in the managing VRO doctor's data entry work section 820 and enable the managing VRO doctor to interact with and work in VRO platform 111. The GUI for the managing VRO doctor's screen 800 can also include a managing VRO doctor's image viewing section 830 through which the managing VRO doctor can view, evaluate, edit, and create images of patient information to which the managing VRO doctor has the proper access level permission in VRO platform 111. For example, the images can include, but are not limited to, a patient's x-rays (i.e., FMS and bitewings), past dental records, 3-D images molds of the patient's teeth and mouth, 3-D images of aligners, and digital designs for the sets of aligners. Lastly, for this embodiment, the GUI for the managing VRO doctor's screen 800 can also include a managing VRO doctor's communication section 840 through which the managing VRO doctor can communicate with the managing VRO doctor's patients as well as the other doctors, and suppliers who are working with the managing VRO doctor's individual patients in the single secure environment.

Alternatively, in FIG. 8, some or all of the functionality of the above-described managing VRO doctor's GUI sections 810, 820, 830, and 840 can be implemented in separate screens or windows as well as in popup window screens.

Figure 9:
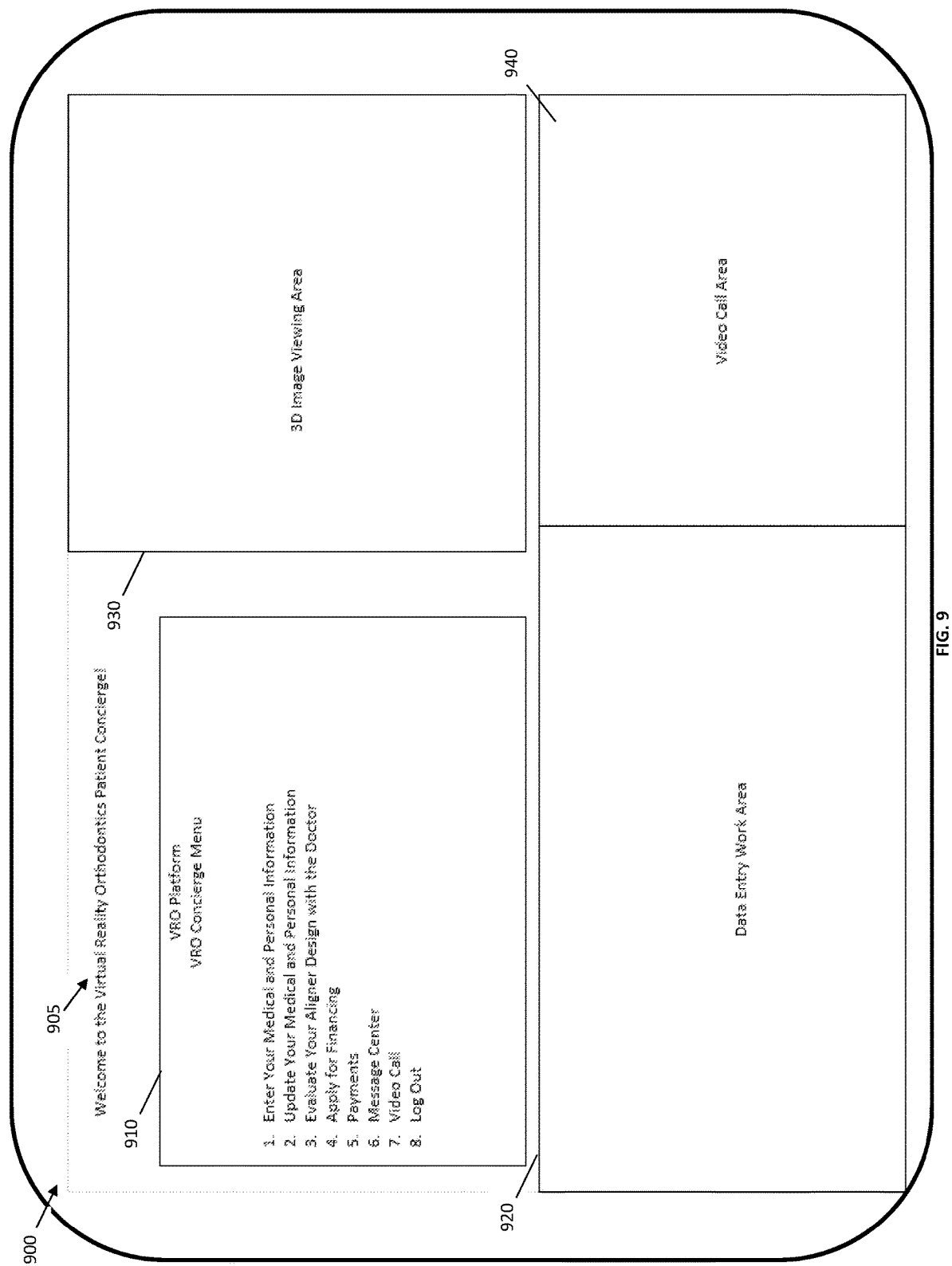
FIG. 9 is a block diagram showing a functional configuration of a GUI screen for a patient from the VRO platform for registering, being diagnosed, provided and treated with clear aligners, and monitored during the treatment with the clear aligners to correct the patient' tooth malocclusions, in accordance with various embodiments of the disclosed subject matter.

FIG. 9 is a block diagram showing a functional configuration of a GUI screen 900 for a patient from VRO platform for registering, being diagnosed, provided and treated with the clear aligners, and monitored during the treatment with the clear aligners to correct the patient' tooth malocclusions, in accordance with various embodiments of the disclosed subject matter. In FIG. 9, the GUI screen 900 for the patient can include a personalized welcome message 905 based on the individual patient's login credentials, which also determines the configuration of a patient's menu section 910, a patient system access level, and access to only the patient's information in VRO platform 111. A patient will only have access to their own patient information in VRO platform 111. The listed menu options, which in FIG. 9 include, for example, but are not limited to, selections to: enter new patient medical and personal information; update existing patient medical and personal information; evaluate the patient's aligner design; apply for financing; make payments; access a central message center through which all permitted other users can be contacted, participate in video calls; and log out of in VRO platform 111. These options are merely illustrative of some of the possible options and in no way should be construed as limiting the options that can be implemented for the patient to use and access VRO platform 111.

In FIG. 9, also included in the GUI for the patient's screen 900 can be a patient's data entry work section 920 through which the patient can enter their patient medical and personal information in VRO platform 111. For example, one or more of the menu options can be opened in the patient's data entry work section 920 and enable the patient to interact with and work in VRO platform 111. The GUI for the patient's screen 900 can also include a patient's image viewing section 930 through which the patient can view and evaluate images of the patient's information in VRO platform 111. For example, the images can include, but are not limited to, a patient's x-rays, past dental records, 3-D images molds of the patient's teeth and mouth, 3-D images of aligners, and digital designs for the sets of aligners. Lastly, for this embodiment, the GUI for the patient's screen 900 can also include a patient's communication section 940 through which the patient can communicate with the patient's doctor(s) and VRO concierge 210 the single secure environment.

Alternatively, in FIG. 9, some or all of the functionality of the above-described patient's GUI sections 910, 920, 930, and 840 can be implemented in separate screens or windows as well as in popup window screens.

Figure 10:
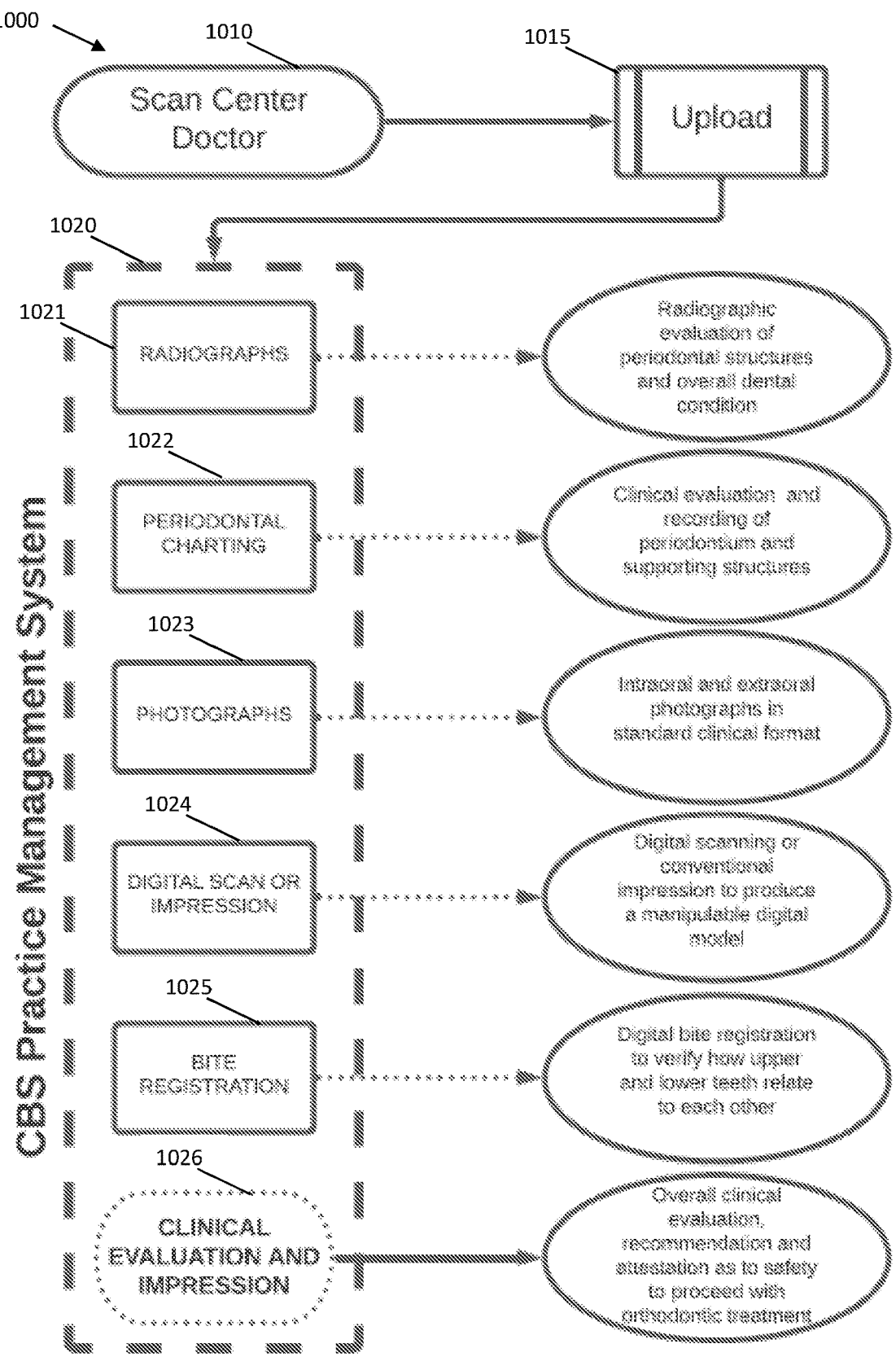
FIG. 10 is a process flow diagram that shows the types of patient information that, for example, but is not limited to what, a doctor, for example, a scan center doctor can upload into the integrated patient platform, in accordance with various embodiments of the disclosed subject matter.

FIG. 10 is a process flow diagram that shows the types of patient information 1020 that, for example, but is not limited to what, a doctor, for example, a scan doctor 1010 can upload 1015 into the integrated patient platform 110, in accordance with various embodiments of the disclosed subject matter. In FIG. 9, this patient information 1020 can include, but is not limited to: radiographs 1021, which can include a radiographic evaluation of periodontal structures and overall dental condition; periodontal charting 1022, which can include clinical evaluation and recording of periodontium and supporting structures; photographs 1023, which can include intraoral and extraoral photographs in standard clinical format; digital scans or impressions 1024, which can include editable and manipulable 3-D images created from digital scanning or conventional impressions; a bite registration 1025, which can include a digital bite registration to verify how the upper and lower teeth relate to each other; and the doctor's clinical evaluation and impression 1026, which can include the doctor's overall clinical evaluation, recommendation and attestation as to safety to proceed with orthodontic treatment.

FIG. 11A is a flow chart diagram of a patient diagnostic and treatment method 1100, in accordance with various embodiments of the disclosed subject matter. In FIG. 11A, the method 1100, which can include a method 1100 for treating a patient suffering from tooth position malocclusion, which can also be referred to as tooth position abnormalities, with removable teeth aligners, starts 1101 by a) receiving 1103 information about the patient tooth position malocclusion condition through a graphical user interface in an integrated patient platform and b) storing 1105, through the integrated patient platform, the information about the patient tooth position malocclusion condition in at least one standardized format in a patient dental record in one or more network-based non-transitory storage devices having a collection of patient dental records stored thereon, the information about the patient tooth position malocclusion condition including one or more three-dimensional (3-D) images of the mouth and teeth of the patient. The at least one standardized formats can vary based on the type of file being stored and, in general are neutral, so non-proprietary, and can include, for example, but are not limited to: for an audio file the file format could be an MP3, a FLAC, a WAV; for a video file the file format could be an MP4, a MOV, an AVI, a WebM; for a 3-D CAD file the file format could be a STL, a DAE, a IGES, a STEP, a VRML/X3D; for image files the file format could be a JPEG, a PNG, a GIF, a TIFF, a PSD, a PDF, an AI; for text the file format could be a DOC, a RTF, a DOCX; and for medical record files the format could be a CDA (Clinical Document Architecture), a CCR (Continuity of Care Record), a CCD (Continuity of Care Document), a CCDA (Consolidated Clinical Document Architecture). The method 1100 continues by c) providing 1107, through the integrated patient platform, access to a number of users over a network, based on an individual user's assigned access rights; d) enabling 1109 each of the number of users, based on the individual user's assigned access right, to review and update certain information the patient dental record with the information about the patient tooth position malocclusion condition in the collection of dental records in real time through the graphical user interface; and e) if any of the updated information about the patient tooth position malocclusion condition is provided in a non-standardized format, then converting 1111, by a content server, the updated information about the patient tooth position malocclusion condition in the non-standardized format into updated information about the patient tooth position malocclusion condition in the standardized format.

In FIG. 11A, the method 1100 continues by f) storing 1113 the updated information about the patient tooth position malocclusion condition in the standardized format in the patient dental record in the one or more network-based non-transitory storage devices; g) receiving and storing 1115 an initial diagnosis that the patient tooth position malocclusion condition is correctable from a first dental professional user in the patient dental record; and h) receiving and storing 1117 a confirmatory diagnosis that the patient tooth position malocclusion condition is correctable from a second dental professional user in the patient dental record. The method 1100 continues by i) receiving and storing 1119, in the patient dental record, designs for a prescribed set of progressive aligners based on the one or more 3-D images of the mouth and teeth of the patient that are configured to progressively correct the patient tooth position malocclusion condition; j) sending 1121 an order message with the designs for the prescribed set of progressive aligners based on the one or more 3-D images of the mouth and teeth of the patient to an aligner manufacturer to manufacture the set of progressive aligners; and k) receiving 1123 a completed order message that the prescribed set of progressive aligners are complete and have been shipped to an approving orthodontist for review and approval.

Figure 11B:
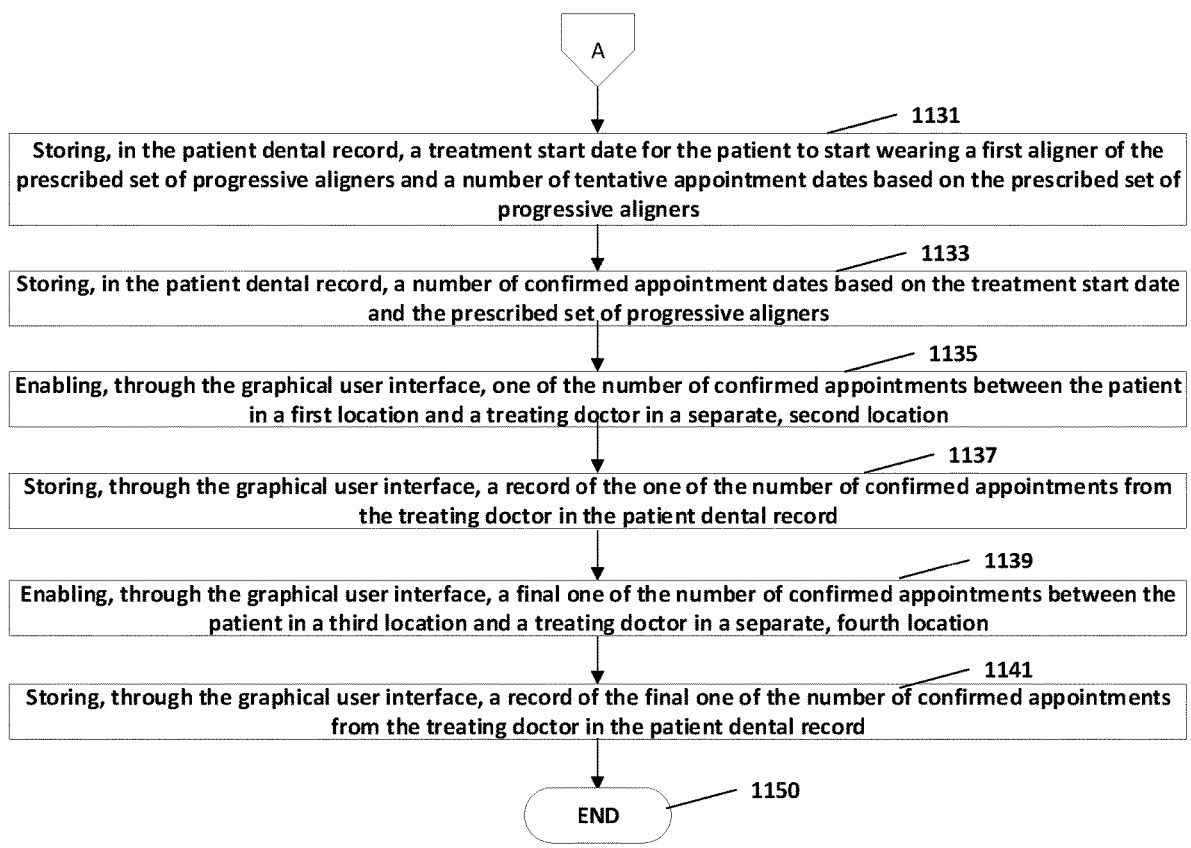

In FIG. 11A, the method 1100 continues by l) receiving 1125 an approval message for the prescribed set of progressive aligners from the approving orthodontist; m) automatically generating 1127, by the content server, a ready message containing updated information about the approval message for the prescribed set of progressive aligners; and n) transmitting 1129 the ready message containing the updated information to at least the first dental professional, the patient, and the aligner manufacturer in real time, so that each of the users has immediate notice of the updated information. The method 1100 continues through off page connector A onto FIG. 11B.

In FIG. 11B, the method 1100 continues by o) storing 1131, in the patient dental record, a treatment start date for the patient to start wearing a first aligner of the set of prescribed aligners and a plurality of tentative appointment dates based on the prescribed set of progressive aligners; p) storing 1133, in the patient dental record, a plurality of confirmed appointment dates based on the treatment start date and the set of prescribed aligners; q) enabling 1135 one of the plurality of confirmed appointments between the patient in a first location and a treating doctor in a separate, second location; and r) storing 1137 a record of the one of the plurality of confirmed appointments from the treating doctor in the patient dental record.

In FIG. 11B, the method 1100 continues by s) enabling 1139 a final appointment from the plurality of confirmed appointments between the patient in a third location and the treating doctor in a separate, fourth location to confirm the patient is to now start wearing a final one of the prescribed set of aligners; and t) storing 1141 a record of the final appointment from the treating doctor in the patient dental record in the one or more network-based non-transitory storage devices. Although not explicitly shown, the method can store at least one post-treatment appointment in the patient dental record in the one or more network-based non-transitory storage devices. The first and the third locations can either be the same or different, physical locations, which is one of the many benefits of the presently disclosed subject matter, because the patient is able to have a virtual appointment with the treating doctor from anywhere the patient can connect to the Internet and login into the integrated patient platform. Likewise, the second and the fourth locations can either be the same or different, physical locations, which is another of the many benefits of the presently disclosed subject matter, because the treating doctor is able to have a virtual appointment with the patient from anywhere the treating doctor can connect to the Internet and login into the integrated patient platform.

In various embodiments of the presently disclosed subject matter, a method for treating a patient with removable teeth aligners, wherein the patient is suffering from tooth position abnormalities, includes determining whether the patient has a correctable tooth position abnormality by: obtaining or having obtained a mold (for example, but not limited to, a traditional dental mold) or a 3D image of the mouth and teeth of the patient; and performing or having performed an analysis of the mold or image of the mouth and teeth of the patient by a first licensed dental professional (for example, but not limited to, a licensed dentist or a licensed orthodontist) to determine whether the patient qualifies with a healthy dentition and has a correctable tooth position abnormality. If the first licensed dental professional determines the patient has the healthy dentition and has the correctable tooth position abnormality, verifying or having verified by a second licensed dental professional the first licensed dental professional's determination that the patient has the correctable tooth position abnormality. If the second licensed dental professional verifies the first licensed dental professional's determination that the patient has the correctable tooth position abnormality, then: if the patient correctable tooth position abnormality is determined to be a minor abnormality, providing a plurality of minor differently configured, removable teeth aligners based on the mold or image of the mouth and teeth of the patient, which are each to be administered to the teeth of the patient for one to two weeks and for at least 20 hours/day; or, if the patient correctable tooth position abnormality is determined to be a major abnormality, then providing a plurality of major differently configured, removable teeth aligners based on the mold of the mouth and teeth of the patient, which are each to be administered to the teeth of the patient for one to two weeks and for at least 20 hours/day.

Finally, if it is determined that the patient has the correctable tooth position abnormality, then upon completion of the administering of each of either the plurality of minor differently configured, removable teeth aligners, or the plurality of major differently configured, removable teeth aligners, providing a final removable teeth aligner based at least partially on the mold of the mouth and teeth of the patient and which is to be administered to the teeth of the patient for at least 12 hours per day and lifetime wear.

Alternatively, it may be determined that the patient condition is too complex use aligners alone, but may qualify for a hybrid treatment regime that includes an initial course of treatment using traditional braces and wire therapy followed by the use of either the plurality of minor differently configured, removable teeth aligners or the plurality of major differently configured, removable teeth aligners.

In various embodiments of the presently disclosed subject matter, a method for treating a patient with removable teeth aligners and braces and wire therapy, wherein the patient is suffering from tooth position abnormalities includes determining whether the patient has a correctable tooth position abnormality by: obtaining or having obtained a digital 3-dimensional mold or an image of the mouth and teeth of the patient; and performing or having performed an analysis of the digital 3-dimensional mold or the image of the mouth and teeth of the patient by a first licensed dental professional to determine whether the patient qualifies with a healthy dentition and has a correctable tooth position abnormality; if the first licensed dental professional determines the patient has the healthy dentition and has the correctable tooth position abnormality, verifying or having verified by a second licensed dental professional the first licensed dental professional's determination that the patient has the healthy dentition and has the correctable tooth position abnormality; if the second licensed dental professional verifies the first licensed dental professional's determination that the patient has the healthy dentition and has the correctable tooth position abnormality, then: if the patients correctable tooth position abnormality is determined to be a minor abnormality, providing a first plurality of differently configured, removable teeth aligners based on the digital 3-dimensional mold of the mouth and teeth of the patient, which are each to be administered to the teeth of the patient for one to two weeks and for at least 20 hours/day; or, if the patient's correctable tooth position abnormality is determined to be greater than a major abnormality, then, first, affixing braces and wires to the patient's teeth for a predetermined prescribed amount of time and then at the end of the predetermined prescribed amount of time removing the braces and wires, and, second, following the removal of the braces and wires, providing a second plurality of differently configured, removable teeth aligners based on the digital 3-dimensional mold of the mouth and teeth of the patient, which are each to be administered to the teeth of the patient for one to two weeks and for at least 20 hours/day; and if it is determined that the patient has the correctable tooth position abnormality, then upon completion of the administering of each of either the first or the second plurality of differently configured, removable teeth aligners, providing a final removable teeth aligner based on the digital 3-dimensional mold of the mouth and teeth of the patient, which is to be administered to the teeth of the patient for at least 12 hours/day and lifetime wear.

A method for treating a patient with removable teeth aligners, wherein the patient is suffering from tooth position abnormalities, the method including: determining whether the patient has a correctable tooth position abnormality by: obtaining or having obtained a digital 3-dimensional mold of the mouth and teeth of the patient; and performing or having performed an analysis of the digital 3-dimensional mold of the mouth and teeth of the patient by a first licensed dental professional to determine whether the patient has a correctable tooth position abnormality. If the first licensed dental professional determines the patient has the correctable tooth position abnormality, verifying or having verified by a second licensed dental professional the first licensed dental professional's determination that the patient has the correctable tooth position abnormality. If the second licensed dental professional verifies the first licensed dental professional's determination that the patient has the correctable tooth position abnormality, then: if the patient's correctable tooth position abnormality is determined to be a minor abnormality, providing a plurality of minor differently configured, removable teeth aligners based on the digital 3-dimensional mold of the mouth and teeth of the patient, which are each to be administered to the teeth of the patient for one to two weeks and for at least 20 hours/day, and if the patient's correctable tooth position abnormality is determined to be a major abnormality, then providing a plurality of major differently configured, removable teeth aligners based on the digital 3-dimensional mold of the mouth and teeth of the patient, which are each to be administered to the teeth of the patient for a predetermined length of time, for example, but not limited to, one to two weeks and for at least 20 hours/day. If it is determined that the patient has the correctable tooth position abnormality, then upon completion of the administering of either the plurality of minor differently configured, removable teeth aligners or the plurality of major differently configured, removable teeth aligners, providing a final removable teeth aligner based at least partially on the digital 3-dimensional mold of the mouth and teeth of the patient, which is to be administered to the teeth of the patient for a predetermined length of time, for example, but not limited to, at least 12 hours/day and lifetime wear.

In various embodiments of the presently disclosed subject matter a method for treating a patient with removable teeth aligners, wherein the patient is suffering from tooth position abnormalities, the method including: a) receiving information about a patient tooth position malocclusion condition through a graphical user interface in an integrated patient platform; b) storing, through the integrated patient platform, the information about the patient tooth position malocclusion condition in at least one standardized format in a patient dental record in one or more network-based non-transitory storage devices having a collection of patient dental records stored thereon, the information about the patient tooth position malocclusion condition including one or more three-dimensional (3-D) images of the mouth and teeth of the patient; c) providing, through the integrated patient platform, access to a plurality of users over a network. based on an individual user's assigned access rights; d) enabling each of the plurality of users, based on the individual user's assigned access right, to review and update the patient dental record with the information about the patient tooth position malocclusion condition in the collection of dental records in real time through the graphical user interface; e) if any of the updated information about the patient tooth position malocclusion condition is provided in a non-standardized format, then converting, by a content server, the updated information about the patient tooth position malocclusion condition in the non-standardized format into updated information about the patient tooth position malocclusion condition in the standardized format; f) storing the updated information about the patient tooth position malocclusion condition in the standardized format in the patient dental record in the one or more network-based non-transitory storage devices; g) receiving and storing an initial diagnosis that the patient tooth position malocclusion condition is correctable from a first dental professional user in the patient dental record; h) receiving and storing a confirmatory diagnosis that the patient tooth position malocclusion condition is correctable from a second dental professional user in the patient dental record; i) receiving and storing, in the patient dental record, designs for a prescribed set of progressive aligners based on the one or more 3-D images of the mouth and teeth of the patient that are configured to progressively correct the patient tooth position malocclusion condition; j) sending an order message with the designs for the prescribed set of progressive aligners based on the one or more 3-D images of the mouth and teeth of the patient to an aligner manufacturer to manufacture the set of progressive aligners; k) receiving a completed order message that the prescribed set of progressive aligners are complete and have been shipped to an approving orthodontist for review and approval; l) receiving an approval message for the prescribed set of progressive aligners from the approving orthodontist; m) automatically generating, by the content server, a ready message containing updated information about the approval message for the prescribed set of progressive aligners; n) transmitting the ready message containing the updated information to at least the first dental professional, the patient, and the aligner manufacturer in real time, so that each of the users has immediate notice of the updated information; o) storing, in the patient dental record, a treatment start date for the patient to start wearing a first aligner of the set of prescribed aligners and a plurality of tentative appointment dates based on the prescribed set of progressive aligners; p) storing, in the patient dental record, a plurality of confirmed appointment dates based on the treatment start date and the set of prescribed aligners; q) enabling one of the plurality of confirmed appointments between the patient in a first location and a treating doctor in a separate, second location; r) storing a record of the one of the plurality of confirmed appointments from the treating doctor in the patient dental record; s) enabling a final appointment from the plurality of confirmed appointments between the patient in a third location and the treating doctor in a separate, fourth location to confirm the patient is to now start wearing a final one of the prescribed set of aligners; and t) storing a record of the final appointment from the treating doctor in the patient dental record in the one or more network-based non-transitory storage devices.

A method for diagnosing, providing aligners for, and treating patient tooth malocclusions including: providing an integrated treatment platform configured to be used by patients, dental professionals, dental service providers, and dental device manufacturers for diagnosing, providing aligners for, and treating patient tooth malocclusions; and using the integrated treatment platform to directly onboard patients through direct marketing efforts, enable dental professionals and dental service providers to enter their patients into the integrated treatment platform to be diagnosed with, provided aligners for, and treated for patient tooth malocclusions. The method further including determining through the integrated treatment platform whether a patient has a correctable tooth position abnormality by: obtaining or having obtained through the integrated treatment platform a digital 3-dimensional mold of the mouth and teeth of the patient; and performing or having performed through the integrated treatment platform an analysis of the digital 3-dimensional mold of the mouth and teeth of the patient by a first licensed dental professional to determine whether the patient has a correctable tooth position abnormality. The method further including if the first licensed dental professional determines the patient has the correctable tooth position abnormality, verifying or having verified by a second licensed dental professional through the integrated treatment platform the first licensed dental professional's determination that the patient has the correctable tooth position abnormality; and if the second licensed dental professional verifies the first licensed dental professional's determination that the patient has the correctable tooth position abnormality, then: if the patient correctable tooth position abnormality is determined to be a minor abnormality, then: creating through the integrated treatment platform a 3-dimensional design for a plurality of a plurality of minor differently configured, removable teeth aligners based on the digital 3-dimensional mold of the mouth and teeth of the patient; and providing through the integrated treatment platform the plurality of minor differently configured, removable teeth aligners based on the digital 3-dimensional mold of the mouth and teeth of the patient, which are each to be administered to the teeth of the patient for a first predetermined number of days and for a first predetermined number of hours per day. Alternatively, if the patient correctable tooth position abnormality is determined to be a major abnormality, then: creating through the integrated treatment platform a 3-dimensional design for a plurality of major differently configured, removable teeth aligners based on the digital 3-dimensional mold of the mouth and teeth of the patient; sending through the integrated treatment platform the 3-dimensional design for the plurality of major differently configured, removable teeth aligners to an aligner manufacturer, so the aligner manufacturer can manufacture on the aligner manufacturer's equipment the plurality of major differently configured, removable teeth aligners based on the 3-dimensional design; sending through the integrated treatment platform a notice that a physical set of the plurality of major differently configured, removable teeth aligners based on the 3-dimensional design are complete and are being sent to a third licensed dental professional for a quality review and approval; approving through the integrated treatment platform by the third licensed dental professional of the physical set of the plurality of major differently configured, removable teeth aligners; and providing through the integrated treatment platform the plurality of major differently configured, removable teeth aligners based on the digital 3-dimensional mold of the mouth and teeth of the patient, which are each to be administered to the teeth of the patient for a second predetermined number of days and for a second predetermined number of hours per day. The method further including: if it is determined that the patient has the correctable tooth position abnormality, then upon completion of the administering of either the plurality of minor differently configured, removable teeth aligners or the plurality of major differently configured, removable teeth aligners, providing through the integrated treatment platform a final removable teeth aligner based at least partially on the digital 3-dimensional mold of the mouth and teeth of the patient, which is to be administered to the teeth of the patient for a third predetermined number of hours/day and lifetime wear.

A method for treating a patient with removable teeth aligners, wherein the patient is suffering from tooth position abnormalities, the method including: determining whether the patient has a correctable tooth position abnormality by: obtaining or having obtained a digital 3-dimensional mold of the mouth and teeth of the patient; and performing or having performed an analysis of the digital 3-dimensional mold of the mouth and teeth of the patient by a first licensed dental professional to determine whether the patient has the correctable tooth position abnormality. If the first licensed dental professional determines the patient has the correctable tooth position abnormality, verifying or having verified, by a second licensed dental professional, the first licensed dental professional's determination that the patient has the correctable tooth position abnormality; and if the second licensed dental professional verifies the first licensed dental professional's determination that the patient has the correctable tooth position abnormality, then: if the patient correctable tooth position abnormality is determined to be a minor correctable tooth position abnormality, providing a plurality of minor differently configured, removable teeth aligners based on the digital 3-dimensional mold of the mouth and teeth of the patient, which are each to be administered to the teeth of the patient for one to two weeks and for at least 20 hours/day, and if the patient correctable tooth position abnormality is determined to be a major correctable tooth position abnormality, then providing a plurality of major differently configured, removable teeth aligners based on the digital 3-dimensional mold of the mouth and teeth of the patient, which are each to be administered to the teeth of the patient for one to two weeks and for at least 20 hours/day; and if it is determined that the patient has the correctable tooth position abnormality, then upon completion of the administering of either the plurality of minor differently configured, removable teeth aligners or the plurality of major differently configured, removable teeth aligners, providing a final removable teeth aligner based at least partially on the digital 3-dimensional mold of the mouth and teeth of the patient, which is to be administered to the teeth of the patient for at least 12 hours/day and lifetime wear.

A method for treating a patient with removable teeth aligners and braces and wire therapy, wherein the patient is diagnosed as suffering from tooth position abnormalities, the method including: determining whether the patient has a correctable tooth position abnormality by: obtaining or having obtained a digital 3-dimensional mold or an image of the mouth and teeth of the patient; and performing or having performed an analysis of the digital 3-dimensional mold or the image of the mouth and teeth of the patient by a first licensed dental professional to determine whether the patient qualifies with a healthy dentition and has the correctable tooth position abnormality. The method also includes: if the first licensed dental professional determines the patient has the healthy dentition and has the correctable tooth position abnormality, verifying or having verified, by a second licensed dental professional, the first licensed dental professional's determination that the patient has the healthy dentition and has the correctable tooth position abnormality; if the second licensed dental professional verifies the first licensed dental professional's determination that the patient has the healthy dentition and has the correctable tooth position abnormality, then: if the patient correctable tooth position abnormality is determined to be a minor abnormality, providing a first prescribed plurality of differently configured, removable teeth aligners based on the digital 3-dimensional mold of the mouth and teeth of the patient, which are each to be administered to the teeth of the patient for one to two weeks and for at least 20 hours/day; or, if the patient correctable tooth position abnormality is determined to be a major correctable tooth position abnormality, providing a second prescribed plurality of differently configured, removable teeth aligners based on the digital 3-dimensional mold of the mouth and teeth of the patient, which are each to be administered to the teeth of the patient for one to two weeks and for at least 20 hours/day; or, if the patient correctable tooth position abnormality is determined to be greater than the major abnormality, then, first, affixing braces and wires to the patient's teeth for a predetermined prescribed amount of time and then at an end of the predetermined prescribed amount of time removing the braces and wires, and, second, following the removal of the braces and wires, providing a third prescribed plurality of differently configured, removable teeth aligners based on the digital 3-dimensional mold of the mouth and teeth of the patient, which are each to be administered to the teeth of the patient for one to two weeks and for at least 20 hours/day; and if it is determined that the patient has the correctable tooth position abnormality, then upon completion of the administering of each of either the first prescribed plurality of differently configured, removable teeth aligners, the second prescribed plurality of differently configured, removable teeth aligners, or the third prescribed plurality of differently configured, removable teeth aligners, providing a final removable teeth aligner based on the digital 3-dimensional mold of the mouth and teeth of the patient, which is to be administered to the teeth of the patient for at least 12 hours/day and lifetime wear.

A method for treating a patient suffering from tooth position abnormalities, the method including: a) receiving information about a patient tooth position malocclusion condition through a graphical user interface in an integrated patient platform; b) storing, through the integrated patient platform, the information at least one standardized format about the patient tooth position malocclusion condition in at least one standardized format in a patient dental record in one or more network-based non-transitory storage devices having a collection of patient dental records stored thereon, the information about the patient tooth position malocclusion condition including one or more three-dimensional (3-D) images of the mouth and teeth of the patient; c) providing, through the integrated patient platform, access to a plurality of users over a network, based on an individual user's assigned access rights; d) enabling each of the plurality of users, based on each of the individual user's assigned access rights, to review and update the patient dental record with updated information about the patient tooth position malocclusion condition in the collection of dental records in real time through the graphical user interface; e) if any of the updated information about the patient tooth position malocclusion condition is provided in a non-standardized format, then converting, by a content server, the updated information about the patient tooth position malocclusion condition in the non-standardized format into updated information about the patient tooth position malocclusion condition in the standardized format; f) storing the updated information about the patient tooth position malocclusion condition in the standardized format patient tooth position malocclusion in the patient dental record in the one or more network-based non-transitory storage devices; g) receiving and storing an initial diagnosis that the patient tooth position malocclusion condition is correctable from a first dental professional user in the patient dental record; h) receiving and storing a confirmatory diagnosis that the patient tooth position malocclusion condition is correctable from a second dental professional user in the patient dental record; i) receiving and storing, in the patient dental record, designs for a prescribed set of progressive aligners based on the one or more 3-D images of the mouth and teeth of the patient that are configured to progressively correct the patient tooth position malocclusion condition; j) sending an order message with the designs for the prescribed set of progressive aligners based on the one or more 3-D images of the mouth and teeth of the patient to an aligner manufacturer to manufacture the set of progressive aligners; k) receiving a completed order message that the prescribed set of progressive aligners are complete and have been shipped to an approving orthodontist for review and approval; l) receiving an approval message for the prescribed set of progressive aligners from the approving orthodontist; m) automatically generating, by the content server, a ready message containing updated information about the approval message for the prescribed set of progressive aligners; n) transmitting the ready message containing the updated information about the approval message for the prescribed set of progressive aligners to at least the first dental professional, the patient, and the aligner manufacturer in real time, so that each of the users has immediate notice of the updated information; o) storing, in the patient dental record, a treatment start date for the patient to start wearing a first aligner of the set of prescribed aligners and a plurality of tentative appointment dates based on the prescribed set of progressive aligners; p) storing, in the patient dental record, a plurality of confirmed appointment dates based on the treatment start date and the set of prescribed aligners; q) enabling one of the plurality of confirmed appointments between the patient in a first location and a treating doctor in a separate, second location; r) storing a record of the one of the plurality of confirmed appointments from the treating doctor in the patient dental record; s) enabling a final appointment from the plurality of confirmed appointments between the patient in a third location and the treating doctor in a separate, fourth location to confirm the patient is to now start wearing a final one of the prescribed set of aligners; and t) storing a record of the final appointment from the treating doctor in the patient dental record in the one or more network-based non-transitory storage devices.

A system for use in treating tooth position malocclusion abnormalities, the system including: an integrated patient platform including a first processor, a memory connected to a first processor, a set of executable instructions stored in the memory that, when executed by the first processor generate a graphical user interface configured to enable and control user access to the integrated patient platform; and a practice management system platform connected to the integrated patient platform, the practice management system platform including a second processor connected to the memory, the set of executable instructions, when executed by the first processor or the second processor, configure the integrated patient platform to: a) receive information about a patient tooth position malocclusion condition; b) store information about the patient tooth position malocclusion condition, through the graphical user interface, in at least one standardized format in a patient dental record in one or more network-based non-transitory storage devices having a collection of patient dental records stored thereon, the information including one or more three-dimensional (3-D) images of the mouth and teeth of the patient; c) provide, through the graphical user interface, access to a plurality of users over a communication network so, based on an individual user's assigned access rights, each of the plurality of users can review and update the patient dental record with the information about the patient tooth position malocclusion condition in the collection of dental records in real time; d) enable each of the plurality of users, based on each of the individual user's assigned access rights, to review and update the patient dental record with the information about the patient tooth position malocclusion condition in the collection of dental records in real time through the graphical user interface; if any of the updated information is provided in a non-standardized format, then convert, by the first processor, the updated information in the non-standardized format into updated information in the standardized format; e) store, in the patient dental record in the memory, the updated information in the standardized format; f) store, in the patient dental record, an initial diagnosis that the patient tooth position malocclusion condition is correctable from a first dental professional user; g) store, in the patient dental record, a confirmatory diagnosis that the patient tooth position malocclusion condition is correctable from a second dental professional user; h) store, in the patient dental record, designs for a prescribed set of progressive aligners based on the one or more 3-D images of the mouth and teeth of the patient that are configured to progressively correct the patient tooth position malocclusion condition; i) send, from the first processor, an order message with the designs for the prescribed set of progressive aligners based on the one or more 3-D images of the mouth and teeth of the patient to an aligner manufacturer to manufacture the set of progressive aligners; j) receive, by the first processor, a completed order message that the prescribed set of progressive aligners are complete and have been shipped to an approving orthodontist for review and approval; k) receive, by the first processor, an approval message for the prescribed set of progressive aligners from the approving orthodontist; l) automatically generate, by the first processor, a ready message containing the updated information about the approval message for the prescribed set of progressive aligners by the content server; m) transmit, from the first processor, the ready message containing the updated information to at least the first dental professional, the patient, and the aligner manufacturer in real time, so that each of the users has immediate notice of the updated information; n) store, in the patient dental record, a treatment start date for the patient to start wearing a first aligner of the set of prescribed aligners and a plurality of tentative appointment dates based on the prescribed set of progressive aligners; o) store, in the patient dental record, a plurality of confirmed appointment dates based on the treatment start date and the set of prescribed aligners; p) enable, through a communication system connected to the first processor, one of the plurality of confirmed appointments between the patient and a treating doctor, where the patient and the treating doctor are in separate locations; q) store, in the patient dental record, a record of the one of the plurality of confirmed appointments from the treating doctor; r) enable, through the communication system connected to the first processor, a final appointment from the plurality of confirmed appointments between the patient and the treating doctor from separate locations to confirm the patient is to start wearing a final one of the prescribed set of aligners; and s) store, in the patient dental record, a record of the final appointment from the treating doctor.

A method for diagnosing, providing aligners for, and treating tooth position malocclusions including: providing an integrated treatment platform configured to be used by at least one patient, at least one dental professional, at least one dental service provider, and at least one dental device manufacturer for diagnosing, providing aligners for, and treating the at least one patient with tooth position malocclusions; using the integrated treatment platform to directly onboard the at least one patient through direct marketing efforts, enable the at least one dental professional and the at least one dental service provider to enter the at least one patient with tooth position malocclusions into the integrated treatment platform to be diagnosed with, provided aligners for, and treated for the tooth position malocclusions; determining through the integrated treatment platform whether the at least one patient has correctable tooth position malocclusions by: obtaining or having obtained through the integrated treatment platform a digital 3-dimensional mold of the mouth and teeth of the at least one patient; and performing or having performed through the integrated treatment platform an analysis of the digital 3-dimensional mold of the mouth and teeth of the at least one patient by a first licensed dental professional to determine whether the at least one patient has the correctable tooth position malocclusions; if the first licensed dental professional determines the at least one patient has the correctable tooth position malocclusions, verifying or having verified by a second licensed dental professional through the integrated treatment platform the first licensed dental professional determination that the at least one patient has the correctable tooth position malocclusions; and if the second licensed dental professional verifies the first licensed dental professional determination that the at least one patient has the correctable tooth position malocclusions, then: if the at least one patient correctable tooth position malocclusions is determined to be a minor correctable tooth position malocclusions, then: creating through the integrated treatment platform a 3-dimensional design for a plurality of minor differently configured, removable teeth aligners based on the digital 3-dimensional mold of the mouth and teeth of the at least one patient; and providing through the integrated treatment platform the plurality of minor differently configured, removable teeth aligners based on the digital 3-dimensional mold of the mouth and teeth of the at least one patient, which are each to be administered to the teeth of the at least one patient for a first predetermined number of days and for a first predetermined number of hours per day, and if the at least one patient correctable tooth position abnormality is determined to be a major correctable tooth position abnormality, then: creating through the integrated treatment platform a 3-dimensional design for a plurality of major differently configured, removable teeth aligners based on the digital 3-dimensional mold of the mouth and teeth of the at least one patient; sending through the integrated treatment platform the 3-dimensional design for the plurality of major differently configured, removable teeth aligners to an aligner manufacturer, so the aligner manufacturer can manufacture the plurality of major differently configured, removable teeth aligners based on the 3-dimensional design; sending through the integrated treatment platform a notice that a physical set of the plurality of major differently configured, removable teeth aligners based on the 3-dimensional design are complete and are being sent to a third licensed dental professional for a quality review and approval; approving through the integrated treatment platform by the third licensed dental professional of the physical set of the plurality of major differently configured, removable teeth aligners; and providing through the integrated treatment platform the plurality of major differently configured, removable teeth aligners based on the digital 3-dimensional mold of the mouth and teeth of the at least one patient, which are each to be administered to the teeth of the at least one patient for a second predetermined number of days and for a second predetermined number of hours per day; and if it is determined that the at least one patient has the correctable tooth position abnormality, then upon completion of the administering of either the plurality of minor differently configured, removable teeth aligners or the plurality of major differently configured, removable teeth aligners, providing through the integrated treatment platform a final removable teeth aligner based at least partially on the digital 3-dimensional mold of the mouth and teeth of the at least one patient, which is to be administered to the teeth of the at least one patient for a third predetermined number of hours/day and lifetime wear.

While the disclosed subject matter has been described in conjunction with a number of embodiments, it is evident that many alternatives, modifications and variations would be or are apparent to those of ordinary skill in the applicable arts. Accordingly, the applicant intends to embrace all such alternatives, modifications, equivalents, and variations that are within the spirit and scope of the disclosed subject matter described herein.

What is claimed is:

1. A system for treating tooth position abnormalities, the system comprising:
   an integrated patient platform including a first processor, a memory connected to the first processor, a set of executable instructions stored in the memory that, when executed by the first processor generate a graphical user interface configured to enable and control user access to the integrated patient platform; and
   a practice management system platform connected to the integrated patient platform, the practice management system platform including a second processor connected to the memory,
   the set of executable instructions, when executed by the first processor or the second processor, configure the integrated patient platform for:
   a) receiving information about a patient tooth position malocclusion condition through the graphical user interface in the integrated patient platform;
   b) storing, through the integrated patient platform, the information about the patient tooth position malocclusion condition in at least one standardized format in a patient dental record in one or more network-based non-transitory storage devices having a collection of patient dental records stored thereon, the information about the patient tooth position malocclusion condition including one or more three-dimensional (3-D) images of a mouth and teeth of the patient;
   c) providing, through the integrated patient platform, access to a plurality of users over a network, based on an individual user's assigned access rights;
   d) enabling each of the plurality of users, based on each of the individual user's assigned access rights, to review and update the patient dental record with updated information about the patient tooth position malocclusion condition in the collection of dental records in real time through the graphical user interface;
   e) if any of the updated information about the patient tooth position malocclusion condition is provided in a non-standardized format, then converting, by a content server, the updated information about the patient tooth position malocclusion condition in the non-standardized format into updated information about the patient tooth position malocclusion condition in the standardized format;
   f) storing the updated information about the patient tooth position malocclusion condition in the standardized format in the patient dental record in the one or more network-based non-transitory storage devices;
   g) receiving and storing an initial diagnosis that the patient tooth position malocclusion condition is correctable from a first dental professional user in the patient dental record;
   h) receiving and storing a confirmatory diagnosis that the patient tooth position malocclusion condition is correctable from a second dental professional user in the patient dental record;
   i) receiving and storing, in the patient dental record, designs for a prescribed set of progressive aligners based on the one or more 3-D images of the mouth and teeth of the patient that are configured to progressively correct the patient tooth position malocclusion condition;
   j) sending an order message with the designs for the prescribed set of progressive aligners based on the one or more 3-D images of the mouth and teeth of the patient to an aligner manufacturer to manufacture the prescribed set of progressive aligners;
   k) receiving a completed order message that a manufactured prescribed set of progressive aligners are complete and have been shipped to an approving orthodontist for review and approval of the manufactured prescribed set of progressive aligners based on the designs for the prescribed set of progressive aligners and the one or more 3-D images of the mouth and teeth of the patient;
   l) receiving an approval message for the manufactured prescribed set of progressive aligners from the approving orthodontist;
   m) automatically generating, by the content server, a ready message containing updated information about the approval message for the manufactured prescribed set of progressive aligners;
   n) transmitting the ready message containing the updated information about the approval message for the manufactured prescribed set of progressive aligners to at least the first dental professional, the patient, and the aligner manufacturer in real time, so that each of the users has immediate notice of the updated information;
   o) storing, in the patient dental record, a treatment start date for the patient to start wearing a first aligner of the manufactured prescribed set of progressive aligners and a plurality of tentative appointment dates based on the manufactured prescribed set of progressive aligners;
   p) storing, in the patient dental record, a plurality of confirmed appointment dates based on the treatment start date and the manufactured prescribed set of progressive aligners;

q) enabling one of the plurality of confirmed appointments between the patient in a first location and a treating doctor in a separate, second location;

r) storing a record of the one of the plurality of confirmed appointments from the treating doctor in the patient dental record;

s) enabling a final appointment from the plurality of confirmed appointments between the patient in a third location and the treating doctor in a separate, fourth location to confirm the patient is to now start wearing a final one of the manufactured prescribed set of progressive aligners; and t) storing a record of the final appointment from the treating doctor in the patient dental record in the one or more network-based non-transitory storage devices.

2. The system of claim 1, wherein the storing, through the integrated patient platform, the information about the patient tooth position malocclusion condition in the standardized format comprises:

storing, through the integrated patient platform, the information about the patient tooth position malocclusion condition in one of a plurality of supported file formats comprising: a doc, a docx, a rich text format (rtf), a portable document format (pdf), an xls, an xlsx, a bmp, a gif, a jpg, a jpeg, a tif, a tiff, a msg, an eml, an htm, one or more neutral CAD , and one or more proprietary CAD file formats.

3. The system of claim 1, wherein the individual user's assigned access rights limits an individual user's access to specific patients' dental records.

4. The system of claim 1, wherein the storing the initial diagnosis that the patient tooth position malocclusion condition is correctable from the first dental professional user in the patient dental record comprises:

storing whether the patient tooth position malocclusion condition is a minor malocclusion, a major malocclusion, or a greater than major malocclusion.

5. The system of claim 1, wherein the storing the confirmatory diagnosis that the patient tooth position malocclusion condition is correctable from a second dental professional user in the patient dental record comprises:

storing a confirmation that the patient tooth position malocclusion condition is a minor malocclusion, a major malocclusion, or a greater than major malocclusion.

6. The system of claim 1, wherein the storing designs for the prescribed set of progressive aligners based on the one or more 3-D images of the mouth and teeth of the patient that are configured to progressively correct the patient tooth position malocclusion condition in the patient dental record comprises:

enabling, through the graphical user interface, the first dental professional or the second dental professional to digitally design the prescribed set of progressive aligners based on the one or more 3-D images of the mouth and teeth of the patient as a set of 3-D images for the prescribed set of progressive aligners; and storing the set of 3-D images for the prescribed set of progressive aligners in the patient dental record.

7. The system of claim 1, wherein the treating doctor comprises at least one of the first dental professional, the second dental professional, and a referring dental professional.

8. The system of claim 1, wherein the receiving and storing, in the patient dental record, designs for a prescribed set of progressive aligners comprises:

receiving and storing, in the patient dental record, designs for a prescribed set of removable progressive aligners.

9. The system of claim 8, wherein the receiving and storing, in the patient dental record, designs for a prescribed set of progressive aligners further comprises:

receiving and storing, in the patient dental record, a prescribed treatment plan for wearing each of the prescribed set of removable progressive aligners.

10. The system of claim 9, wherein the receiving and storing, in the patient dental record, the prescribed treatment plan for wearing each of the prescribed set of removable progressive aligners further comprises:

receiving and storing, in the patient dental record, the prescribed treatment plan for wearing each of the prescribed set of removable progressive aligners to include wearing each of the prescribed set of removable progressive aligners for one to two weeks and at least 20 hours per day.

11. The system of claim 9, wherein the receiving and storing, in the patient dental record, the prescribed treatment plan for wearing each of the prescribed set of removable progressive aligners further comprises:

receiving and storing, in the patient dental record, the prescribed treatment plan for wearing the final one of the prescribed set of aligners at least 12 hours a day and lifetime wear.

12. The system of claim 1, wherein the enabling one of the plurality of confirmed appointments between the patient in the first location and the treating doctor in the separate, second location further comprises:

enabling the one of the plurality of confirmed appointments between the patient in the first location and the treating doctor in the separate, second location via a video call through the integrated patient platform.

13. A system for use in treating tooth position malocclusion abnormalities, the system comprising:

an integrated patient platform including a first processor, a memory connected to the first processor, a set of executable instructions stored in the memory that, when executed by the first processor generate a graphical user interface configured to enable and control user access to the integrated patient platform; and a practice management system platform connected to the integrated patient platform, the practice management system platform including a second processor connected to the memory, the set of executable instructions, when executed by the first processor or the second processor, configure the integrated patient platform to:

a) receive information about a patient tooth position malocclusion condition;

b) store information about the patient tooth position malocclusion condition, through the graphical user interface, in at least one standardized format in a patient dental record in one or more network-based non-transitory storage devices having a collection of patient dental records stored thereon, the information including one or more three-dimensional (3-D) images of a mouth and teeth of the patient;

c) provide, through the graphical user interface, access to a plurality of users over a communication network so, based on an individual user's assigned access rights, each of the plurality of users can review and update the patient dental record with the information about the patient tooth position malocclusion condition in the collection of dental records in real time;

d) enable each of the plurality of users, based on each of the individual user's assigned access rights, to review and update the patient dental record with the information about the patient tooth position malocclusion condition in the collection of dental records in real time through the graphical user interface; if any of the updated information is provided in a non-standardized format, then convert, by the first processor, the updated information in the non-standardized format into updated information in the standardized format;

e) store, in the patient dental record in the memory, the updated information in the standardized format;

f) store, in the patient dental record, an initial diagnosis that the patient tooth position malocclusion condition is correctable from a first dental professional user;

g) store, in the patient dental record, a confirmatory diagnosis that the patient tooth position malocclusion condition is correctable from a second dental professional user;

h) store, in the patient dental record, designs for a prescribed set of progressive aligners based on the one or more 3-D images of the mouth and teeth of the patient that are configured to progressively correct the patient tooth position malocclusion condition;

i) send, from the first processor, an order message with the designs for the prescribed set of progressive aligners based on the one or more 3-D images of the mouth and teeth of the patient to an aligner manufacturer to manufacture the prescribed set of progressive aligners;

j) receive, by the first processor, a completed order message that a manufactured prescribed set of progressive aligners are complete and have been shipped to an approving orthodontist for review and approval of the manufactured prescribed set of progressive aligners based on the designs for the prescribed set of progressive aligners and the one or more 3-D images of the mouth and teeth of the patient;

k) receive, by the first processor, an approval message for the manufactured prescribed set of progressive aligners from the approving orthodontist;

l) automatically generate, by the first processor, a ready message containing the updated information about the approval message for the manufactured prescribed set of progressive aligners by a content server;

m) transmit, from the first processor, the ready message containing the updated information to at least the first dental professional, the patient, and the aligner manufacturer in real time, so that each of the users has immediate notice of the updated information;

n) store, in the patient dental record, a treatment start date for the patient to start wearing a first aligner of the manufactured prescribed set of progressive aligners and a plurality of tentative appointment dates based on the manufactured prescribed set of progressive aligners;

o) store, in the patient dental record, a plurality of confirmed appointment dates based on the treatment start date and the manufactured prescribed set of progressive aligners;

p) enable, through a communication system connected to the first processor, one of the plurality of confirmed appointments between the patient and a treating doctor, where the patient and the treating doctor are in separate locations;

q) store, in the patient dental record, a record of the one of the plurality of confirmed appointments from the treating doctor;

r) enable, through the communication system connected to the first processor, a final appointment from the plurality of confirmed appointments between the patient and the treating doctor from separate locations to confirm the patient is to start wearing a final one of the manufactured prescribed set of progressive aligners; and s) store, in the patient dental record, a record of the final appointment from the treating doctor.

14. The system of claim 13, wherein the instructions, when executed by the first processor, further configure the integrated patient platform to:
s) store, in the patient dental record, at least one post-treatment appointment.

15. The system of claim 14, wherein the individual user's assigned access rights limits an individual user's access to specific patient dental records and to certain information in the specific patient dental records.

16. The system of claim 14, wherein the store, in the patient dental record, the initial diagnosis that the patient tooth position malocclusion condition is correctable from the first dental professional user comprises:
store, in the patient dental record, whether the patient tooth position malocclusion condition is a minor malocclusion, a major malocclusion, a greater than major malocclusion, or an uncorrectable malocclusion.

17. The system of claim 14, wherein the store, in the patient dental record, the confirmatory diagnosis that the patient tooth position malocclusion condition is correctable from a second dental professional user:
store, in the patient dental record, a confirmation that the patient tooth position malocclusion condition is a minor malocclusion, a major malocclusion, a greater than major malocclusion, or an uncorrectable malocclusion.

18. The system of claim 14, wherein the store, in the patient dental record, designs for the prescribed set of progressive aligners based on the one or more 3-D images of the mouth and teeth of the patient that are configured to progressively correct the patient tooth position malocclusion condition further comprises:
enabling, through the graphical user interface, the first dental professional, the second dental professional, or a third dental professional to digitally design the prescribed set of progressive aligners prior to the store, in the patient dental record, designs for the prescribed set of progressive aligners.

19. The system of claim 14, wherein the treating doctor comprises at least one of the first dental professional, the second dental professional, and the approving orthodontist.

20. The system of claim 13, wherein the second processor comprises at least one processor.

21. The system of claim 20, wherein the store, in the patient dental record, designs for the prescribed set of progressive aligners based on the one or more 3-D images of the mouth and teeth of the patient that are configured to progressively correct the patient tooth position malocclusion condition the practice management system platform comprises:
creating designs, using the second processor, for the prescribed set of progressive aligners based on the one or more 3-D images of the mouth and teeth of the patient; and
storing, in the patient dental record, the designs for the prescribed set of progressive aligners based on the one or more 3-D images of the mouth and teeth of the patient.

* * * * *